(12) United States Patent
Bothra et al.

(10) Patent No.: US 11,545,260 B1
(45) Date of Patent: Jan. 3, 2023

(54) CHANNEL-SPECIFIC ENGAGEMENT MACHINE LEARNING ARCHITECTURE

(71) Applicant: Express Scripts Strategic Development, Inc., St. Louis, MO (US)

(72) Inventors: Amit K. Bothra, St. Louis, MO (US); Pritesh J. Shah, Paramus, NJ (US); Christopher G. Lehmuth, St. Louis, MO (US); Bradley D. Flynn, St. Louis, MO (US); Varun Tandra, Teaneck, NJ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 181 days.

(21) Appl. No.: 17/095,504

(22) Filed: Nov. 11, 2020

Related U.S. Application Data

(63) Continuation-in-part of application No. 16/731,378, filed on Dec. 31, 2019.
(Continued)

(51) Int. Cl.
*G16H 40/20* (2018.01)
*G06N 3/08* (2006.01)
(Continued)

(52) U.S. Cl.
CPC .......... *G16H 40/20* (2018.01); *A61B 5/4833* (2013.01); *G06N 3/08* (2013.01); *G06Q 10/107* (2013.01);
(Continued)

(58) Field of Classification Search
None
See application file for complete search history.

(56) References Cited

U.S. PATENT DOCUMENTS 8,986,014 B2    3/2015   Murray
9,147,163 B1    9/2015   Nease
(Continued)

OTHER PUBLICATIONS

Wicklin, Should you use principal component regression, Oct. 25, 2017, https://blogs.sas.com/content/iml/2017/10/25/principal-component-regression-drawbacks.html (Year: 2017).*

*Primary Examiner* — Devin C Hein
(74) *Attorney, Agent, or Firm* — Miller Johnson

(57) ABSTRACT

A computer-implemented method includes generating an intervention model for a population of users based on engagement data indicating successfulness of prior interventions for each of the population of users. Each prior intervention corresponds to one of multiple engagement channels, and the intervention model includes multiple channel-specific models. The method includes supplying data related to a first user as input to the intervention model to determine multiple channel-specific intervention expectations. Each channel-specific intervention expectation indicates a likelihood that the first user will take action in response to an intervention being executed using the corresponding engagement channel. The method includes determining a likelihood of a gap in care for the first user, and in response to the gap in care likelihood exceeding a minimum threshold, selecting a first intervention according to the channel-specific intervention expectation that has a highest determined value, and scheduling the selected first intervention for execution.

20 Claims, 18 Drawing Sheets

Related U.S. Application Data

(60) Provisional application No. 62/787,224, filed on Dec. 31, 2018.

(51) Int. Cl.
| | |
|---|---|
| *G06Q 50/00* | (2012.01) |
| *G06Q 30/02* | (2012.01) |
| *G06Q 10/10* | (2012.01) |
| *G16H 20/10* | (2018.01) |
| *G16H 50/30* | (2018.01) |
| *G16H 50/20* | (2018.01) |
| *G16H 50/70* | (2018.01) |
| *A61B 5/00* | (2006.01) |
| *G16H 80/00* | (2018.01) |
| *H04L 65/1066* | (2022.01) |

(52) U.S. Cl.
CPC ......... *G06Q 30/0201* (2013.01); *G06Q 50/01* (2013.01); *G16H 20/10* (2018.01); *G16H 50/20* (2018.01); *G16H 50/30* (2018.01); *G16H 50/70* (2018.01); *G16H 80/00* (2018.01); *H04L 65/1066* (2013.01)

(56) References Cited

U.S. PATENT DOCUMENTS

| | | |
|---|---|---|
| 9,773,094 B1 | 9/2017 | Balagere |
| 10,120,979 B2 | 11/2018 | Ryan |
| 10,140,422 B2 | 11/2018 | Rust |
| 10,872,131 B2 | 12/2020 | Rust |
| 2001/0020229 A1 | 9/2001 | Lash |
| 2008/0275729 A1 | 11/2008 | Taggart |
| 2009/0106004 A1 | 4/2009 | Edwards |
| 2012/0004924 A1 | 1/2012 | Kachnowski |
| 2012/0330676 A1 | 12/2012 | Puckrein |
| 2015/0032465 A1 | 1/2015 | Sundar |
| 2015/0112710 A1 | 4/2015 | Haber |
| 2016/0357923 A1 | 12/2016 | Dong |
| 2017/0024546 A1 | 1/2017 | Schmidt |
| 2017/0177801 A1* | 6/2017 | Ryan ............... G16H 50/30 |
| 2017/0235894 A1 | 8/2017 | Cox |
| 2017/0293733 A1* | 10/2017 | Kelly .............. G16H 50/20 |
| 2018/0039762 A1 | 2/2018 | Schmidt |
| 2019/0065663 A1 | 2/2019 | Rust |
| 2019/0304607 A1 | 10/2019 | Steele |
| 2020/0012897 A1 | 1/2020 | Sreenivasan |
| 2020/0082932 A1* | 3/2020 | Salinas ............. G16H 80/00 |
| 2020/0151627 A1 | 5/2020 | Shukla |

* cited by examiner

CHANNEL-SPECIFIC ENGAGEMENT MACHINE LEARNING ARCHITECTURE

CROSS-REFERENCE TO RELATED APPLICATIONS

This application is a continuation-in-part of U.S. patent application Ser. No. 16/731,378 filed Dec. 31, 2019, which claims the benefit of U.S. Provisional Application No. 62/787,224 filed Dec. 31, 2018. The entire disclosures of the applications referenced above are incorporated by reference.

FIELD

The present disclosure relates to medical interventions and more particularly to systems and methods for user intervention to increase prescription adherence.

BACKGROUND

When a user (also referred to as a patient) is prescribed medication for a condition, successful treatment of that condition requires following the prescription schedule. In other words, the user must fill the prescription, follow the dosage instructions, and then refill the prescription as necessary. Deviating from the dosage and refill instructions is referred to as non-adherence.

According to some estimates, non-adherence results in $300 billion of medical waste every year. This medical waste may include drugs dispensed but not taken, an increase in medical practitioner visits, and, most particularly, an increase in acute episodes that are much more expensive to treat.

Because of the increased cost and worse patient outcomes caused by non-adherence, providers in the medical space (including health insurers and pharmacy benefit managers) may perform interventions (also referred to as outreach) with users. These interventions may take the form of physical visits, phone calls, emails, texts, mobile alerts, etc. However, with limited resources, frequent personal outreach to every user may not be possible. Therefore, there is a need to develop better intervention systems to achieve more positive patient outcomes.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer-implemented method includes generating an intervention model for a population of users based on contact data for each of the population of users, demographic data for each of the population of users, and engagement data indicating successfulness of prior interventions for each of the population of users. Each prior intervention corresponds to one of multiple engagement channels, and the intervention model includes multiple channel-specific models, each corresponding to a respective one of the multiple engagement channels. The method includes, for a first user of the population of users, obtaining first data related to the first user. The first data includes at least one of contact data of the first user, demographic data of the first user, and engagement data indicating successfulness of prior interventions with the first user, and each prior intervention with the first user is associated with one of the multiple engagement channels. The method includes supplying the obtained first data as input to the intervention model to determine multiple channel-specific intervention expectations. Each channel-specific intervention expectation indicates a likelihood that the first user will take action in response to an intervention being executed using the engagement channel corresponding to the channel-specific intervention expectation. The method includes determining a likelihood of a gap in care for the first user, and in response to the gap in care likelihood exceeding a minimum threshold, selecting a first intervention according to the channel-specific intervention expectation that has a highest determined value, and scheduling the selected first intervention for execution.

In other features, the multiple engagement channels include at least two of a real-time communication with the first user by a specialist, a call to the first user by an automated call system, an email to the first user, and a text message to the first user. In other features, at least one of the multiple engagement channels includes multiple intervention options within the engagement channel, selecting the first intervention includes selecting a first one of the multiple intervention options within the engagement channel that has a highest intervention expectation among the intervention options, and scheduling the first intervention includes scheduling the selected first one of the multiple intervention options within the engagement channel.

In other features, the intervention model includes a channel-agnostic intervention model that determines a general intervention expectation indicating a likelihood that the first user will take action in response to any intervention being executed using any of the engagement channels, and in response to the general intervention expectation being below a specified threshold, the method includes initiating a low engagement intervention process and identifying at least one reason for low engagement of the first user.

In other features, the method includes, in response to determining that a time elapsed since a most recent intervention for the first user is less than a specified delay threshold, waiting until the specified delay threshold has elapsed prior to selecting the first intervention. In other features, the method includes identifying one or more targets relevant to the first user, determining a measure of progress toward at least one of the identified targets, determining an engagement importance metric based on the determined measure of progress, and weighting the channel-specific intervention expectations according to the determined engagement importance metric prior to selecting the first intervention.

In other features, scheduling the first intervention includes, in response to determining that the measure of progress is less than a specified minimum threshold, scheduling an intervention corresponding to the channel-specific intervention expectation that has a highest determined value prior to weighting. In other features, the method includes determining a cost of engagement for each of the multiple engagement channels, determining a channel capacity for each of the multiple engagement channels, and weighting the channel-specific intervention expectations according to the determined costs of engagement and channel capacities prior to selecting the first intervention.

In other features, the method includes determining at least one user adherence factor associated with the first user, and weighting the channel-specific intervention expectations according to the determined user adherence factor prior to selecting the first intervention. In other features, the at least one user adherence factor includes at least one of a prescription refill cost to the first user, a pill burden of the first user, and a comorbidity condition of the first user.

In other features, scheduling the first intervention includes, in response to the comorbidity condition of the first user indicating a future adverse event risk that is higher than a specified threshold, scheduling an intervention corresponding to the channel-specific intervention expectation that has a highest determined value prior to weighting. In other features, the method includes tracking success of the selected first intervention based on a medication possession ratio (MPR). The MPR is calculated as a number of days of a prescription currently in possession of the first user divided by a number of total days initially supplied with the prescription.

A computer system includes memory configured to store computer-executable instructions and an intervention model for a population of users based on contact data for each of the population of users, demographic data for each of the population of users, and engagement data indicating successfulness of prior interventions for each of the population of users. Each prior intervention corresponds to one of multiple engagement channels, and the intervention model includes multiple channel-specific models, each corresponding to a respective one of the multiple engagement channels. The system includes at least one processor configured to execute the instructions. The instructions include, for a first user of the population of users, obtaining first data related to the first user. The first data includes at least one of contact data of the first user, demographic data of the first user, and engagement data indicating successfulness of prior interventions with the first user, and each prior intervention with the first user is associated with one of the multiple engagement channels. The instructions include supplying the obtained first data as input to the intervention model to determine multiple channel-specific intervention expectations. Each channel-specific intervention expectation indicates a likelihood that the first user will take action in response to an intervention being executed using the engagement channel corresponding to the channel-specific intervention expectation. The instructions include determining a likelihood of a gap in care for the first user, and in response to the gap in care likelihood exceeding a minimum threshold, selecting a first intervention according to the channel-specific intervention expectation that has a highest determined value, and scheduling the selected first intervention for execution.

In other features, the multiple engagement channels include at least two of a real-time communication with the first user by a specialist, a call to the first user by an automated call system, an email to the first user, and a text message to the first user. In other features, at least one of the multiple engagement channels includes multiple intervention options within the engagement channel, selecting the first intervention includes selecting a first one of the multiple intervention options within the engagement channel that has a highest intervention expectation among the intervention options, and scheduling the first intervention includes scheduling the selected first one of the multiple intervention options within the engagement channel.

In other features, the intervention model includes a channel-agnostic intervention model that determines a general intervention expectation indicating a likelihood that the first user will take action in response to any intervention being executed using any of the engagement channels, and in response to the general intervention expectation being below a specified threshold, the instructions include initiating a low engagement intervention process and identifying at least one reason for low engagement of the first user.

In other features, the instructions further include, in response to determining that a time elapsed since a most recent intervention for the first user is less than a specified delay threshold, waiting until the specified delay threshold has elapsed prior to selecting the first intervention. In other features, the instructions further include identifying one or more targets relevant to the first user, determining a measure of progress toward at least one of the identified targets, determining an engagement importance metric based on the determined measure of progress, and weighting the channel-specific intervention expectations according to the determined engagement importance metric prior to selecting the first intervention.

In other features, scheduling the first intervention includes, in response to determining that the measure of progress is less than a specified minimum threshold, scheduling an intervention corresponding to the channel-specific intervention expectation that has a highest determined value prior to weighting.

In other features, the instructions further include determining a cost of engagement for each of the multiple engagement channels, determining a channel capacity for each of the multiple engagement channels, and weighting the channel-specific intervention expectations according to the determined costs and channel capacities prior to selecting the first intervention.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Figure 1:
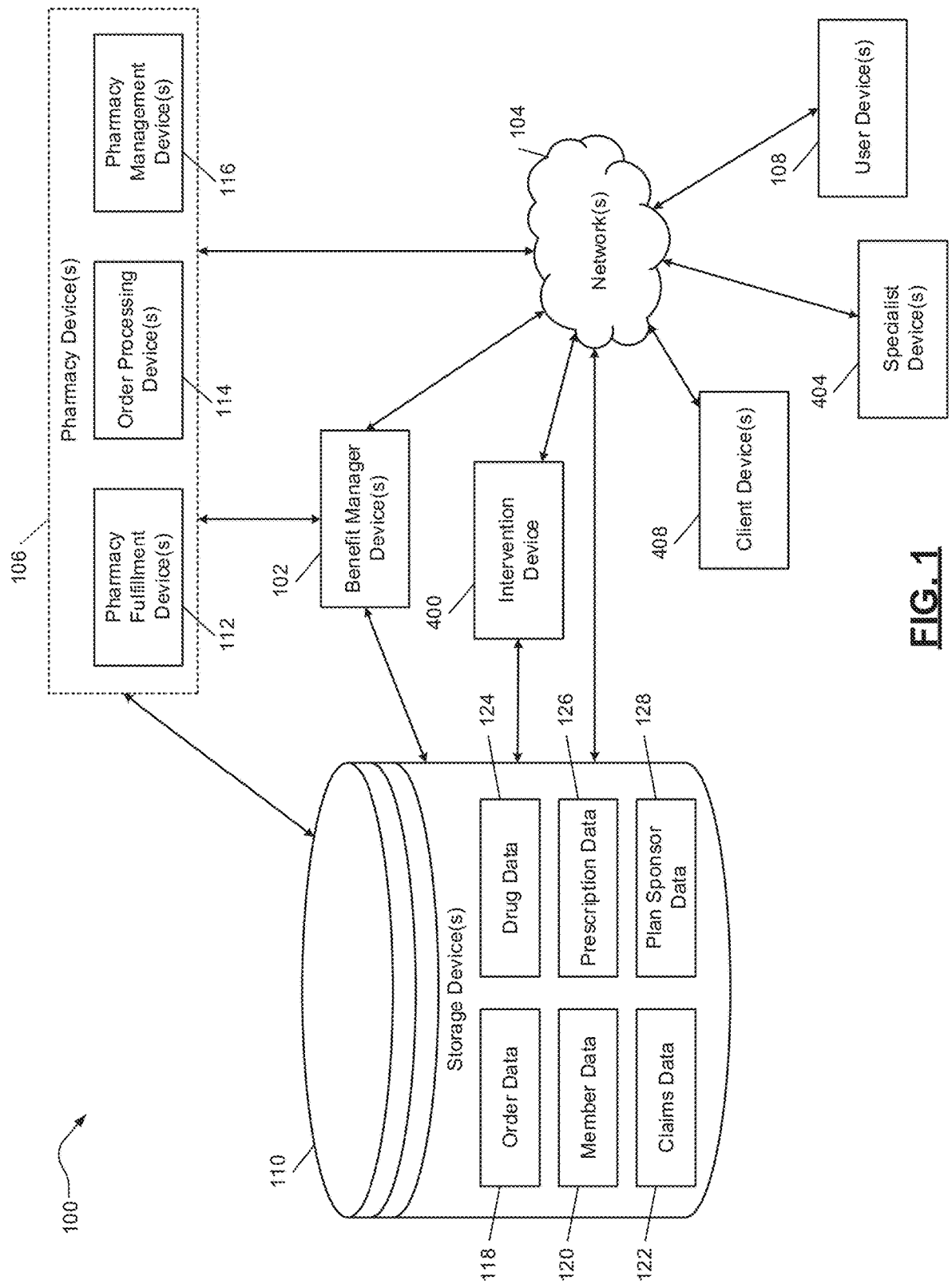
FIG. 1 is a functional block diagram of an example system including a high-volume pharmacy.

The present disclosure describes how an operator in the medical space can use an intervention system to identify users for whom interventions are necessary and to select the appropriate interventions for specific users. Interventions may be warranted when it appears likely that there will be a gap in care, such as a medication running out prior to conclusion of a treatment regimen. In one specific example, a gap in care is experienced when a user exhausts their supply of prescription pills prior to obtaining a refill of the prescription.

Interventions may take the form of an operator in the medical space (such as a health insurer or a pharmacy benefit manager) contacting the user. For example, an operator may directly contact the user or request that a local pharmacy, medical provider, or caregiver contact the user. These contacts may take the form of personal visits, telephone calls, text messages, mobile alerts, emails, postal letters, etc. Communications with the user may include reminders about their course of treatment, including expected dates by which existing medication will be exhausted, expired, or otherwise need refilling.

The communications may also include warnings about the potential effects of a gap in care. The communications may provide incentives for the user to avoid a gap in care, such as discounts on drugs, free shipping, or discounts on expedited shipping. In addition, the communications may assist the user in setting up automatic refills and other technological approaches to increasing adherence. Another technological approach to increase adherence is establishing mail-order prescriptions, which may reduce the time and transportation barriers to obtaining new and refill prescriptions from a retail pharmacy.

In addition to choosing between these types of interventions, specifics about the interventions may be determined. For example, a time of day at which to make the intervention may be specified. In addition, when multiple contact methods are available, the type of contact (such as work email, home phone, etc.) may be selected along with the time of day and day of week for the intervention.

A system according to the present disclosure identifies which users are at risk of a gap in care and also how receptive the users will be to interventions. In this way, interventions can be targeted to have maximum impact. In some implementations, the cost or patient outcome associated with non-adherence may be taken into account so that interventions can be directed to those users where non-adherence has a more drastic negative outcome for the patient and/or may incur a higher cost in treatment due to a gap in care.

As one example only, a two-by-two matrix may be used to select interventions, with users at high risk of a gap in care and a high likelihood of engagement with an intervention will receive a real-time indication (such as a phone call). Meanwhile, users at high risk of a gap in care but a low likelihood of engagement with an intervention may receive a physical letter with a discount code for mail-ordering a prescription. Users with a lower risk of a gap in care may receive a text message, regardless of whether their likelihood of engagement is high or low. In other words, in this particular example of potential business logic, two of the cells in this matrix are assigned the same intervention. Users whose risk of a gap in care is low enough receive no intervention at all and are therefore not reflected in this matrix.

In other implementations, a single score may be determined based on two or more of (i) risk of gap in care, (ii) likelihood of engagement, and (iii) cost of gap in care. Then, ranges of this single score are assigned various interventions. Values of the single score below a certain threshold (for example, indicating both a low risk of a gap in care as well as a low likelihood of engagement with interventions) may be assigned no intervention.

A variety of models may be implemented to estimate risks of a gap in care. In various implementations, multiple models may be implemented and one or more models may be selected based on user data. For example, a first model may estimate the risk of a user experiencing a gap in care related to treatment for diabetes. A second model may estimate a risk of a gap in care for treatment related to hypertension. A third model may estimate a risk of a gap in care for treatment of high cholesterol. A fourth model may estimate a risk of a high figure of merit being measured (such as A1C for a diabetic). A fifth model may estimate a risk of a user not obtaining a lab test for a particular condition (such as a blood test for ongoing diabetes management).

Meanwhile, a general intervention model may be implemented to determine the likelihood of a user engaging with an executed intervention. The intervention model may be agnostic to the condition of the patient, meaning that the intervention model is applicable to patients having diabetes, hypertension, high cholesterol, multiple of or none of those conditions. In addition, the intervention model may be agnostic to the type (or, channel) of engagement. In other words, the intervention model provides an estimate of the user engaging with an intervention regardless of the form of the intervention (such as a phone call or an email).

In some implementations, additional specific models may be implemented. For example, models may be implemented that are specific to the medical condition of the user. For example, a diabetes model may be implemented for diabetic users. Meanwhile, a hypertension model may be implemented for hypertensive users and a lipid model may be implemented for users with high cholesterol. A priority ranking system may select which model is applied to the user that has multiple conditions. In other implementations, all applicable models may be applied to the user and a single score calculated based on a weighted combination or a voting scheme.

In various implementations, channel-specific intervention models may be developed. These channel-specific intervention models may assess the likelihood that the user will engage with, for example, a phone call versus an email. Some of these models may be restricted to specific users or to specific populations or groups of users. When multiple of the models apply to a specific user, different engagement scores may be determined for a single user and are then used to determine which intervention to execute for that user.

Based on the risk models and intervention models, an operator can determine which users require intervention and select the appropriate interventions for the users. The operator can then queue these interventions, such as by scheduling emails for transmission and adding phone calls to a schedule for specialists (such as pharmacists). As these interventions are performed (such as emails being sent or calls being made), the fact of the intervention as well as the feedback from the user regarding intervention is logged.

In addition, over time, the success of the intervention may be tracked based on whether the user fills required prescriptions within a timely manner. One objective measure of success may be medication possession ratio (MPR), which may be calculated by the number of days of a prescription currently in the user's possession divided by the number of total days initially supplied with the prescription. A higher MPR indicates that the user is less likely to exhaust their supply of the drug.

A client of the operator, such as a health plan or medical practitioner, may access data about executed interventions (transmitted emails, placed phone calls, etc.) for their users. A web portal may allow the client (such as a health insurance representative) to review past interventions, execute their own interventions (such as placing a call to the user's phone number), and log the interventions performed by the client. In addition, the client may be able to access data about the likelihood of engagement by the user so that the client can make their own decisions, based on business logic, regarding executing interventions for particular users.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy benefit but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
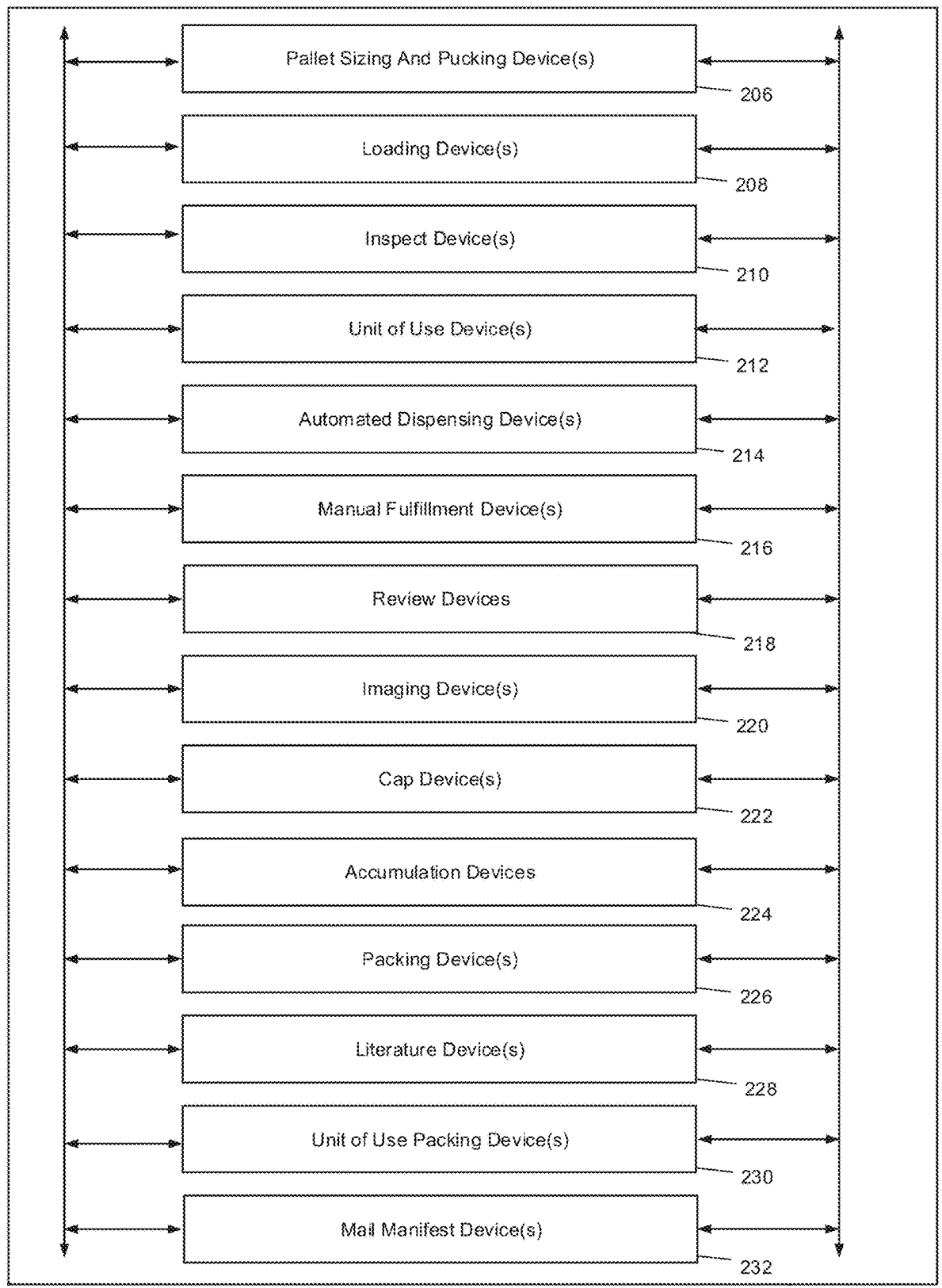
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device (s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
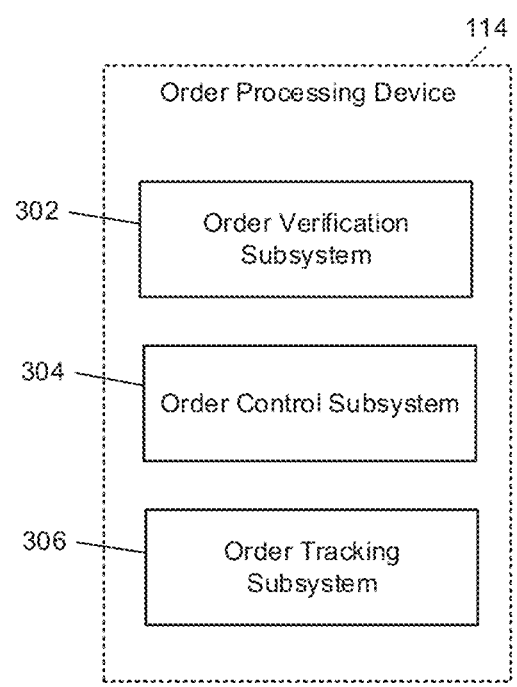
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Intervention System Block Diagrams

Returning to FIG. 1, the member data 120 may also include health data about the user, such as conditions the user is diagnosed with, such as hypertension, high cholesterol, or diabetes. An intervention device 400 obtains data from the storage devices 110 and may communicate with the user devices 108, specialist devices 404, and client devices 408 via networks 104. The specialist devices 404 may include pharmacists and pharmacist technicians that may execute interventions, such as placing phone calls to users. The client devices 408 may be operated by clients, such as representatives of health insurers.

Figure 4:
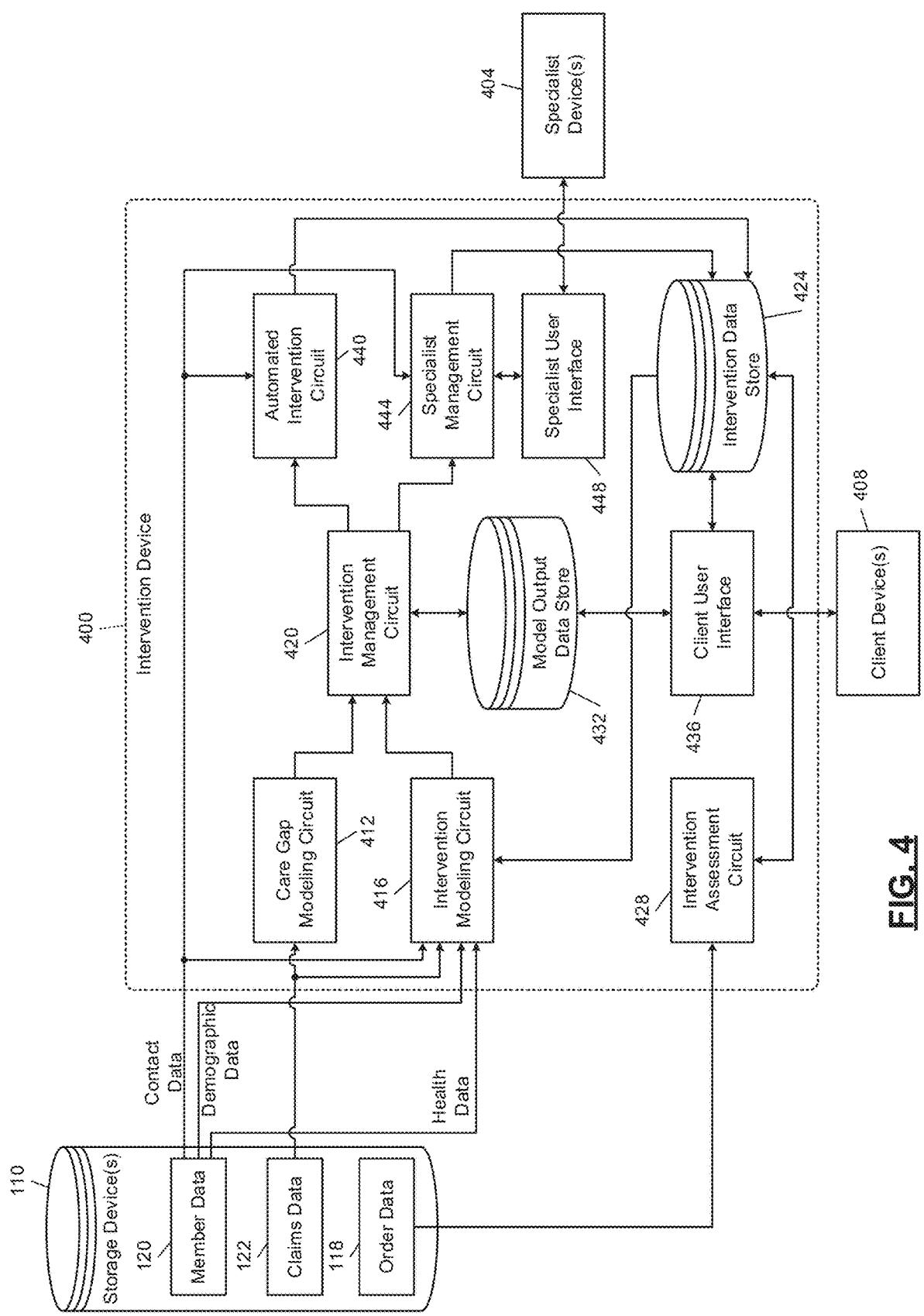
FIG. 4 is a functional block diagram of an example implementation of an intervention device according to the principles of the present disclosure.

In FIG. 4, an example implementation of the intervention device 400 includes a care gap modeling circuit 412 and an intervention modeling circuit 416. The care gap modeling circuit 412 develops a model indicating a likelihood of risk for a user, such as a risk of a gap in care. These estimations are provided to an intervention management circuit 420. The intervention modeling circuit 416 develops a model of the likelihood of user engagement with interventions in general or specific interventions. These intervention engagement data are provided to the intervention management circuit 420.

The intervention modeling circuit 416 may receive, as inputs to the model, the claims data 122 for a specific user, demographic data of the user, contact data of the user, and health data of the user. The care gap modeling circuit 412 may also receive these inputs—for illustration purposes, the care gap modeling circuit 412 is shown in FIG. 4 as receiving just the claims data 122. Contact data may include whether particular forms of contact (such as an email address) are present and may also include more granular information, such as the domain of the email address. Demographic data may include, as examples, age and gender.

The claims data 122 may indicate historical data of when prescriptions were filled and may include information about intervals between refills. The intervention modeling circuit 416 also receives information about past interventions from an intervention data store 424. The intervention data store 424 tracks prior interventions, including email campaigns, phone calls, etc.

The intervention data store 424 may also store information about intervention outcomes. These outcomes may include verbal feedback provided during phone call and may also include objective success measures from an intervention assessment circuit 428. The intervention assessment circuit 428 may receive the order data 118 and determine whether successes resulted from interventions.

For example, if an order is placed within 30 days of intervention, that may be classified as a success by the intervention assessment circuit 428. In various implementations, the business logic used by the intervention assessment circuit 428 to assess the success or failure of an intervention may be established by the business logic of the organization making the intervention. For example, an intervention that provides a discount for mail-order prescriptions may assess success only in response to receiving a mail-order script and not a retail script.

The intervention management circuit 420 stores care gap expectation data and intervention expectation data for users in a model output data store 432. A client user interface 436, which may be implemented in a web portal, allows the client devices 408 to access some or all of the information related to the care gap expectation data and intervention expectation data. The client user interface 436 may also provide access to information from the intervention data store 424, such as a list of past interventions for a user of interest.

The intervention management circuit 420 determines whether intervention is needed for a user and also determines the appropriate intervention. The intervention management circuit 420 assigns interventions to, in the example of FIG. 4, an automated intervention circuit 440 or a specialist management circuit 444. The automated intervention circuit 440 transmits automated interventions to users, such as emails, prerecorded calls, etc. The automated intervention circuit 440 may rely on contact data from the member data 120 and logs the interventions in the intervention data store 424.

The specialist management circuit 444 schedules specialist interactions. For example, specialists may include pharmacists, pharmacy technicians, and call center operators. The specialist management circuit 444 may prioritize and schedule specialist interventions. A specialist user interface 448, which may be implemented as a web portal, indicates to specialists using specialist devices 404 which users to contact. For example, a list of phone numbers to call may be presented to a specialist operating one of the specialist devices 404. The specialist user interface 448 allows the specialist to notate whether and what reaction was provided by the user and may also provide a script for the specialist to follow.

For example purposes only, FIGS. 9A-9E show example scripts that may be presented by the specialist user interface 448. The scripts are presented in flowchart form and may present each rectangle to the specialist as the specialist makes choices such as yes or no. Additional information can be found in U.S. Pat. No. 9,147,163, titled "Methods and systems for improving therapy adherence" and issued Sep. 29, 2015, the entire disclosure of which is incorporated by reference.

Figure 5:
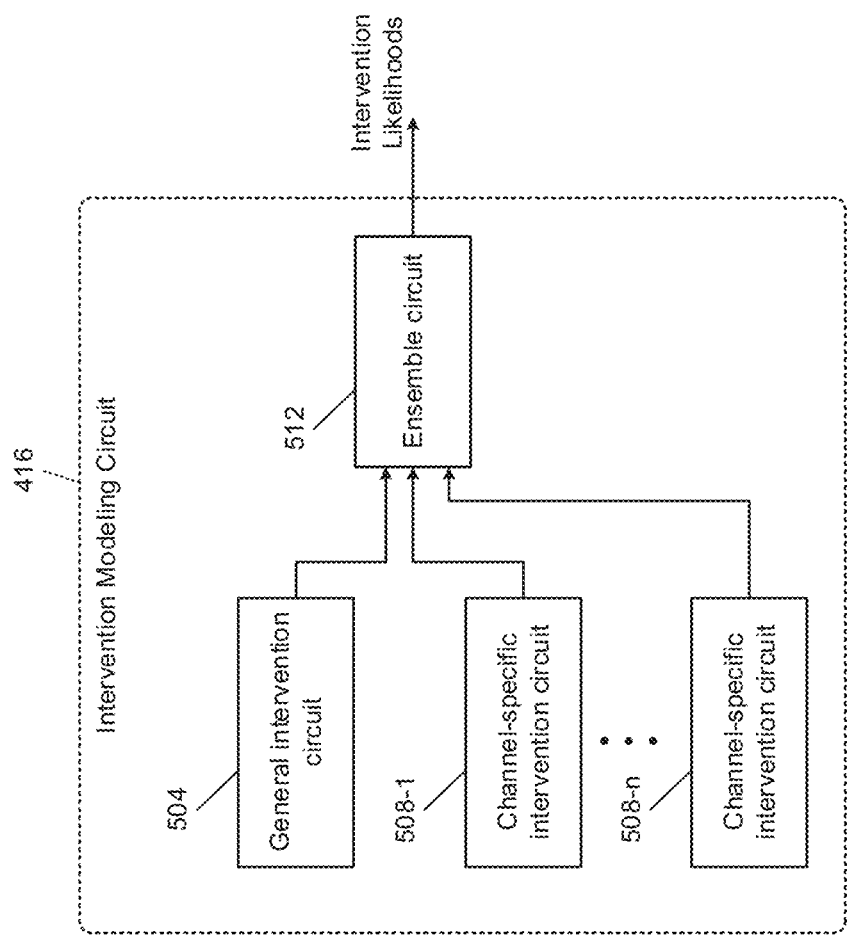
FIG. 5 is a functional block diagram of an example intervention modeling circuit.
Figure 6:
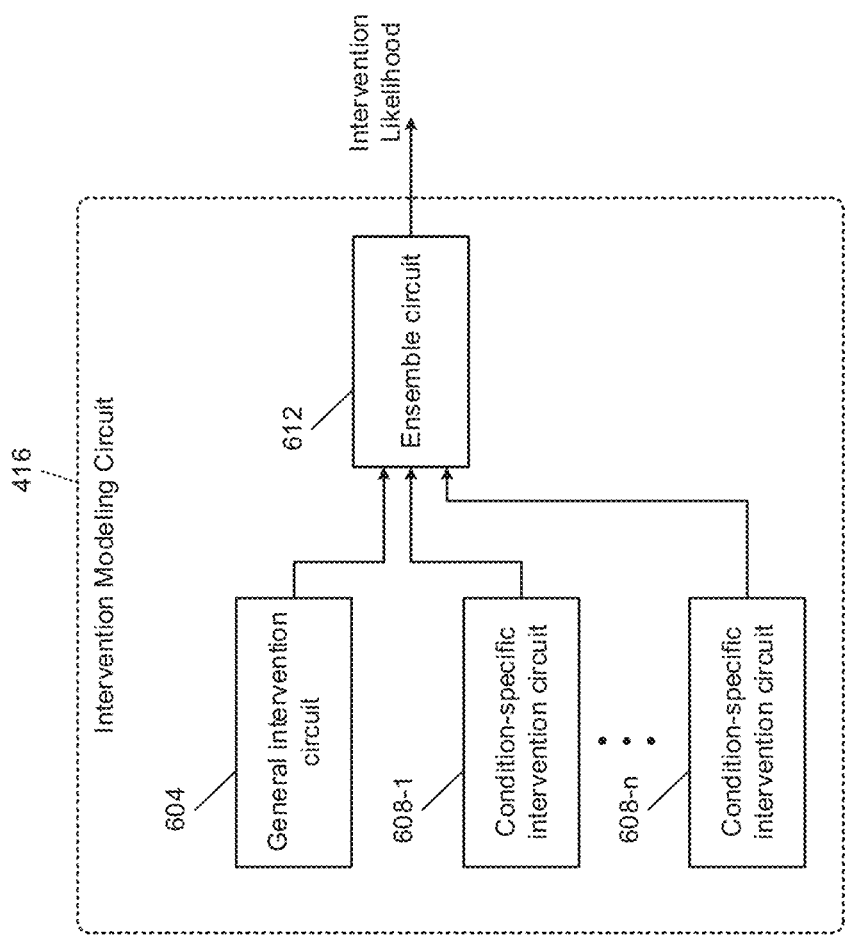
FIG. 6 is a functional block diagram of another example implementation of an intervention modeling circuit.

In FIG. 5, an example implementation of the intervention modeling circuit 416 includes a general intervention circuit 504 that is agnostic to channel of intervention (such as phone call versus text message). In this example, the intervention modeling circuit 416 also includes channel-specific intervention circuits 508-1 . . . 508-*n* (collectively, channel-specific intervention circuits 508). Each of the channel-specific intervention circuits 508 may be specific to a single channel of intervention or a class of intervention. For example, one class of intervention may be real-time, which includes a phone call or online chat, while a second class of intervention includes a unidirectional intervention such as an email, letter, or text message.

An ensemble circuit 512 selects from among the general intervention circuit 504 and the channel-specific intervention circuits 508 and outputs one or more intervention likelihoods. For example, the ensemble circuit 512 may output likelihoods of the user engaging with an intervention for each type of intervention. In other implementations, the ensemble circuit 512 may output a single likelihood of engagement by the user with any executed intervention. The ensemble circuit 512 may select which of the channel-specific intervention circuits 508, if any, are applicable to the user and ignore outputs of those that are not applicable. The ensemble circuit 512 may calculate a weighted average or may select a most applicable output when generating a single likelihood value.

In other implementations, an example implementation of the intervention modeling circuit 416 includes a general intervention circuit 604 that is agnostic to user condition. Meanwhile, the intervention modeling circuit 416 also includes condition-specific intervention circuits 608-1 . . . 608-n (collectively, condition-specific intervention circuits 608) that are specific to conditions or class of conditions that a user may have been diagnosed with.

For example, a first class of condition may include chronic conditions such as diabetes or hypertension. A second class of condition may include acute conditions such as viral or bacterial infections. An ensemble circuit 612 selects and/or combines outputs of the general intervention circuit 604 and the condition-specific intervention circuits 608. The ensemble circuit 612 may generate and output a single intervention likelihood indicating how likely it is that the user will engage with an executed intervention. For example, the intervention likelihood may be a value from 0 to 1, with a 1 indicating that the user is 100% likely to take action in response to an intervention being executed (for example, a text message being sent or a call being placed).

Each of the models in the circuits 504, 508, 604, and 608 may be implemented using a logistic regression classifier based on determined feature vectors. In various implementations, some or all of the models in the circuits 504, 508, 604, and 608 may be implemented using a deep learning architecture (such as convolutional neural networks) that receive raw data not transformed into feature vectors. In various implementations, the deep learning architecture may essentially perform intrinsic feature engineering, ignoring data that is not correlated with engagement outcomes.

Figure 7:
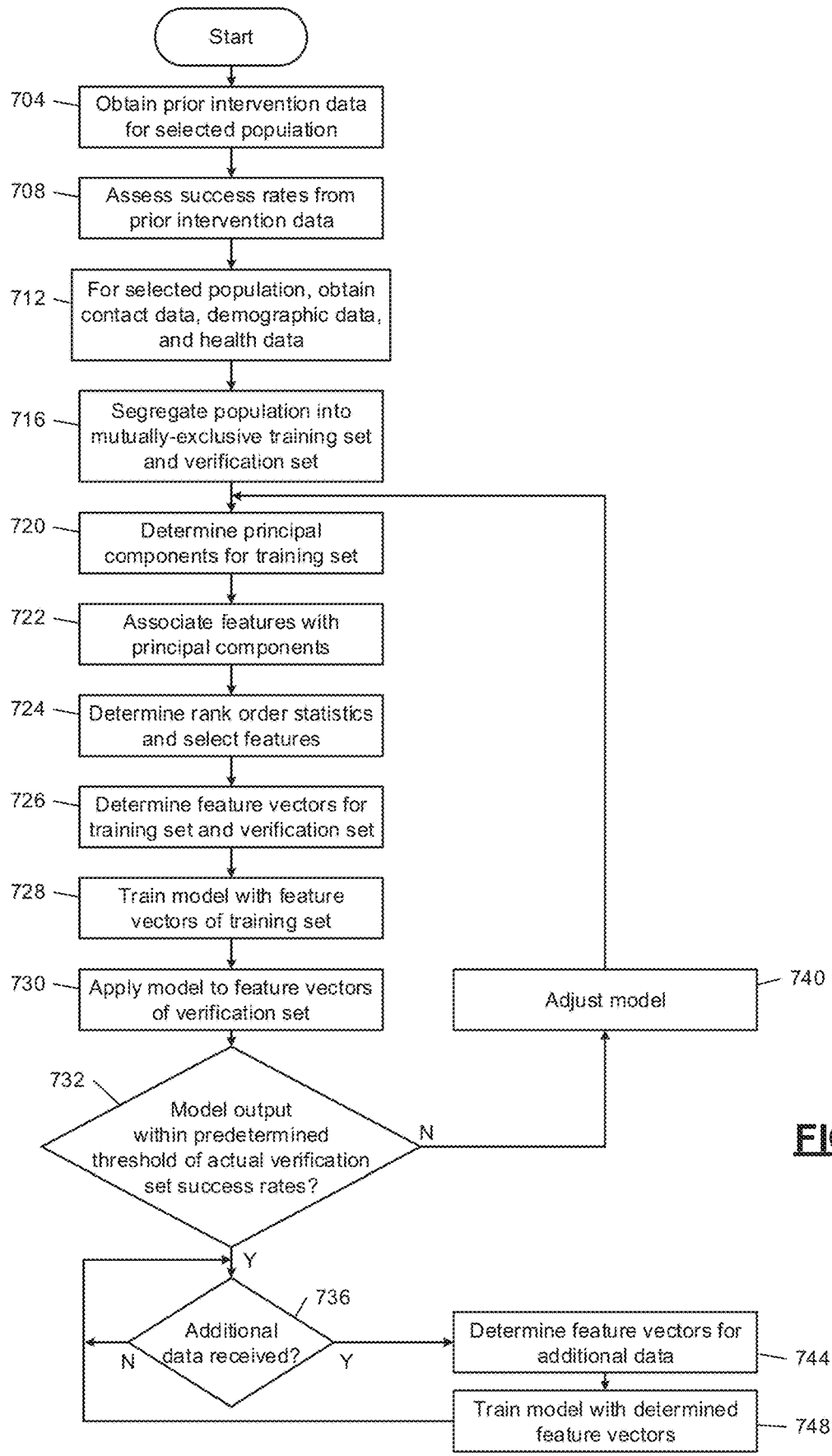
FIG. 7 is a flowchart showing example intervention model creation and maintenance.

In FIG. 7, example operation of model creation and maintenance is shown. Control begins at 704, where for a given population (such as the users corresponding to a particular health plan), data regarding interventions that have been executed in the past is obtained. At 708, control assesses success rates of interventions from the prior intervention data. For example, as discussed above, success may be defined by the manager of the prior interventions. At 712, control obtains contact data, demographic data, and health data for the selected population. At 716, control segregates the population into mutually exclusive sets: a training set of users and a verification set of users.

At 720, control determines principal components for the features of the training set. In various implementations, there may be a large number of features (sometimes called variables) available for the population, which may increase the processing and storage demands of the machine learning models. In addition, creating feature vectors with a large number of features, some of which may not be pertinent, may actually decrease the accuracy of the model.

The number of features (also referred to as dimensionality) may be reduced using a variety of techniques. As one example only, hundreds of features may be narrowed down to thirty or forty features. The technique described in FIG. 7 is principal component analysis (PCA). Specifically, PCA is used to rank order the available features so that a subset can be selected for inclusion in feature vectors. The subset is not necessarily a proper subset—in various implementations, some situations may lead to the selected features including all of the available features.

Traditionally, PCA is used to identify principal components, which are combinations of features (often weighted averages of the constituent features), so that feature vectors can be created based on those principal components. That traditional approach is applicable to the present disclosure. However, in the approach described here with respect to FIG. 7, PCA is used to quantify how well features are correlated with a target space. These quantities allow the features to be ranked and the highest-ranked features are themselves then selected for inclusion in feature vectors.

The principal components are formed from the features using a transformation matrix. In other words, each principal component is a weighted average of all of the features—each element of the transformation matrix describes the weight of a certain feature in generating a certain principal component. In various implementations, the transformation matrix is a square matrix, meaning that the number of principal components is equal to the number of features. However, some of the principal components may have very little significance (contribution to variability) and so may be ignored to reduce dimensionality.

In general terms, principal components explain variance. Features that are highly correlated will be highly weighted in a single principal component. In PCA, the highest-variance-explaining component is the first principal component, the second-highest-variance-explaining component is the second principal component, etc.

As a simplistic example, consider a setting in which three features are present (named x, y, and z) and therefore PCA defines three principal components (pc1, pc2, and pc3). For this example, assume that the transformation matrix derived by PCA is as follows:

TABLE 1

|   | pc1  | pc2 | pc3  |
|---|------|-----|------|
| x | 0.9  | 0.3 | 0.2  |
| y | 0.05 | 0.7 | 0.05 |
| z | 0.05 | 0   | 0.75 |

The transformation matrix describes how a point in feature space can be transformed to a point in principal component space, where dimension pc1 for a point in principal component space is formed by adding 0.9 times the x dimension of the point in feature space, 0.05 times the y dimension of the point in feature space, and 0.9 times the z dimension of the point in feature space. Note that the weights in each column sum to one.

The eigenvalue of each principal component is an indicator of how much variance the principal component explains. Principal components with an eigenvalue of less than a threshold are ignored for the following analysis. In the implementation of FIG. 7, the threshold is 1.0. For example only, assume that the eigenvalues of pc1, pc2, and pc3 are 1.5, 1.2, and 0.7, respectively. Using a threshold of 1.0, pc3 is excluded from further consideration. This leaves the following reduced matrix:

TABLE 2

|   | pc1  | pc2 |
|---|------|-----|
| x | 0.9  | 0.3 |
| y | 0.05 | 0.7 |
| z | 0.05 | 0   |

Next, at 722, the principal component with which each feature is most strongly correlated is identified. Feature x is most strongly correlated with pc1, feature y is most strongly correlated with pc2, and feature z is most strongly correlated with pc3. This may be represented in the transformation matrix as follows, by only retaining values for items in the matrix showing the strongest correlation for each feature.

TABLE 3

|   | pc1  | pc2 |
|---|------|-----|
| x | 0.9  |     |
| y |      | 0.7 |
| z | 0.05 |     |

At 724, control performs a regression analysis for each of the sets of features associated with the remaining principal components. The selection criteria for the regression analysis is to determine which features are more correlated with the model target (for example, likelihood of success of intervention). The first regression test (corresponding to pc1) would include features x and z as predictors, while the second regression test (corresponding to pc2) would include feature y as a predictor.

The regression tests apply backward selection to only keep predictors that are most correlated with the target. Control calculates a Wald statistic for each of x and z:

$$\frac{\hat{\theta} - \theta_0}{se(\hat{\theta})}$$

where B is the maximum likelihood estimate of the feature, $\theta_0$ is the target of the model (again, the observed likelihood of success of intervention), and $se(\hat{\theta})$ is the standard error of the maximum likelihood estimate (MLE) of $\hat{\theta}$. If the Wald statistic has a high value, then the feature is considered to have a significant contribution to the model prediction.

Next, control determines a statistical value (such as a p-value or Z statistic) of the Wald statistic for each feature. If the statistical value is greater than a threshold (for example, if the p-value is greater than 0.05), the feature is excluded. After removing features, the regression test is re-run until no features are removed.

Consider the first regression test, which corresponds to pc1 and includes features x and z. Control calculates a p-value for each of feature x and feature z. Assuming that the p-value for feature z is greater than 0.05, feature z is removed. The regression test is re-run, this time on only feature x. If the p-value of feature x in this iteration is greater than 0.05, feature x would be eliminated from use in feature vectors. In this case, however, assume that the p-value of feature x in this iteration is less than 0.05. As a result, no features would be removed, and the first regression test would be finished.

Following all of the regression tests, the remaining sets of features (which may be the empty set) from each of the regression tests are combined together. And then another regression test is performed on the combination. Backward selection is used to eliminate features from this combination. The backward selection may use p-values and either the same threshold (0.05) or a different threshold. Features with p-values falling above the threshold are removed at each iteration until no features are removed.

The resulting reduced set of features following backward selection determines how feature vectors are created. At 726, control creates feature vectors for the population (both the training set and the verification set) based on the selected features.

At 728, control trains a machine learning model, such as a logistic regression classifier, using selected feature vectors of the training set. At 730, control applies the model to feature vectors of users in the verification set and determines the likelihood of engagement for the users of the verification set. At 732, control compares the predicted engagement of the user's in the verification set with actual historical success rates for the users within the verification set. If the model output is within a predetermined threshold of the actual historical data (such as the average absolute value of deviation being less than a predetermined limit), control transfers to 736; otherwise, control transfers to 740.

At 740, control adjusts the model, such as by adjusting which features are included in the feature vectors or by adjusting other model parameters. Control then returns to 720. Meanwhile, at 736, control waits for additional data to be received. Once additional data is received, control transfers to 744. At 744, control determines feature vectors for the additional data. At 748, control trains the model with the determined feature vectors and returns to 736.

To determine feature vectors at 726, the present disclosure may first reduce the number of features. For each of the variables, especially for continuous variables, there may be nonlinear aspects with respect to the target. So, a variable can be converted into a set of bins. For example, a quantile cut means defining bins such that approximately 5% of the data falls into each bin. In other implementations, the quantile cut means that up to 5% of the data falls into each bin.

As one example, consider a variable such as age, which may range from 18-85 and be approximately Gaussian with a mean around 30 or 40. When rank-ordering the data with respect to age, take the first 5% of the population (the youngest 5%) and define a bin accordingly. Then take the next 5% of the population and define a second bin.

After defining the 20 bins (or some other number if not using a quantile cut), combine all of the population members who do not have a value for the variable into a missing value bin.

Then, determine a probabilistic score (which takes values between 0 and 1) for the target for each bin. For example, determine a percentage indicating how likely the population within each bin is to respond to engagement and/or determine a percentage indicating the adherence of the population within that bin. Then a logit can be calculated from the probabilistic score (p) as follows:

$$\text{logit}(p) = \log\left(\frac{p}{1-p}\right).$$

With a missing value bin and using a quantile cut, there are now 21 bins, each with a logit.

Each feature can therefore be converted into a logit that is fed into a logistic regression model instead of raw values. As one example, an age feature is presented not as the number of years but as the calculated logit. A stepwise selection method can then reduce the set of features down to those that are most correlated with the target—as one example, reducing the number of features from 60 to 8. Then the reduced set of features are used to train the model in 728.

The stepwise selection method may be implemented with a combination of forward selection and backward selection. In backward selection, variables are present in the model and at each step variables are analyzed to see whether they are statistically significant—if not, they are removed as features. Meanwhile, forward selection starts with no features and begins adding only the most statistically significant features.

At each step, control may test whether a variable can be added and whether a variable can be removed. For each variable, control calculates a chi-squared value (or, analogously, a p value) from either the Rao or Wald distribution. For example, in a particular step of the stepwise selection method, control calculates a Rao statistic for each variable not yet in the model (forward selection), expressed as a p value. If the p value of a variable is less than a predetermined threshold for forward selection (alpha threshold), the variable is a candidate for addition to the model. If no variables have p values lower than the alpha threshold, then no variable is added to the model at that step. In various implementations, if there are multiple variables with p values lower than the alpha threshold during a particular step of the stepwise selection method, only the variable with the largest chi-squared value (lowest p value) is added.

Meanwhile, control calculates a Wald statistic for each variable already in the model (backward selection), expressed as a p value. If the p value of a variable currently in the model is greater than a predetermined threshold for backward selection (beta threshold), then the variable is removed from the model. In various implementations, the values of the alpha and beta thresholds may be the same (one numerical example is 0.05). If no variables have p values higher than the beta threshold, then no variable is removed from the model at that step. In various implementations, if there are multiple variables with p values greater than the beta threshold during a particular step of the stepwise selection method, only the variable with the smallest chi-squared value (highest p value) is removed.

In light of the added or removed variables, control refits the logistic regression and performs another step of forward and backward selection. This process is continued until a particular criterion or criteria are reached. For example, the process may be repeated until a specific number of features (as a numerical example, 8) are in the model, until there are no features left to add to the model, after a predetermined number of iterations, etc. The goal is to develop a parsimonious model, which has as few features as possible while still performing well following training (as measured with test data).

Figure 8:
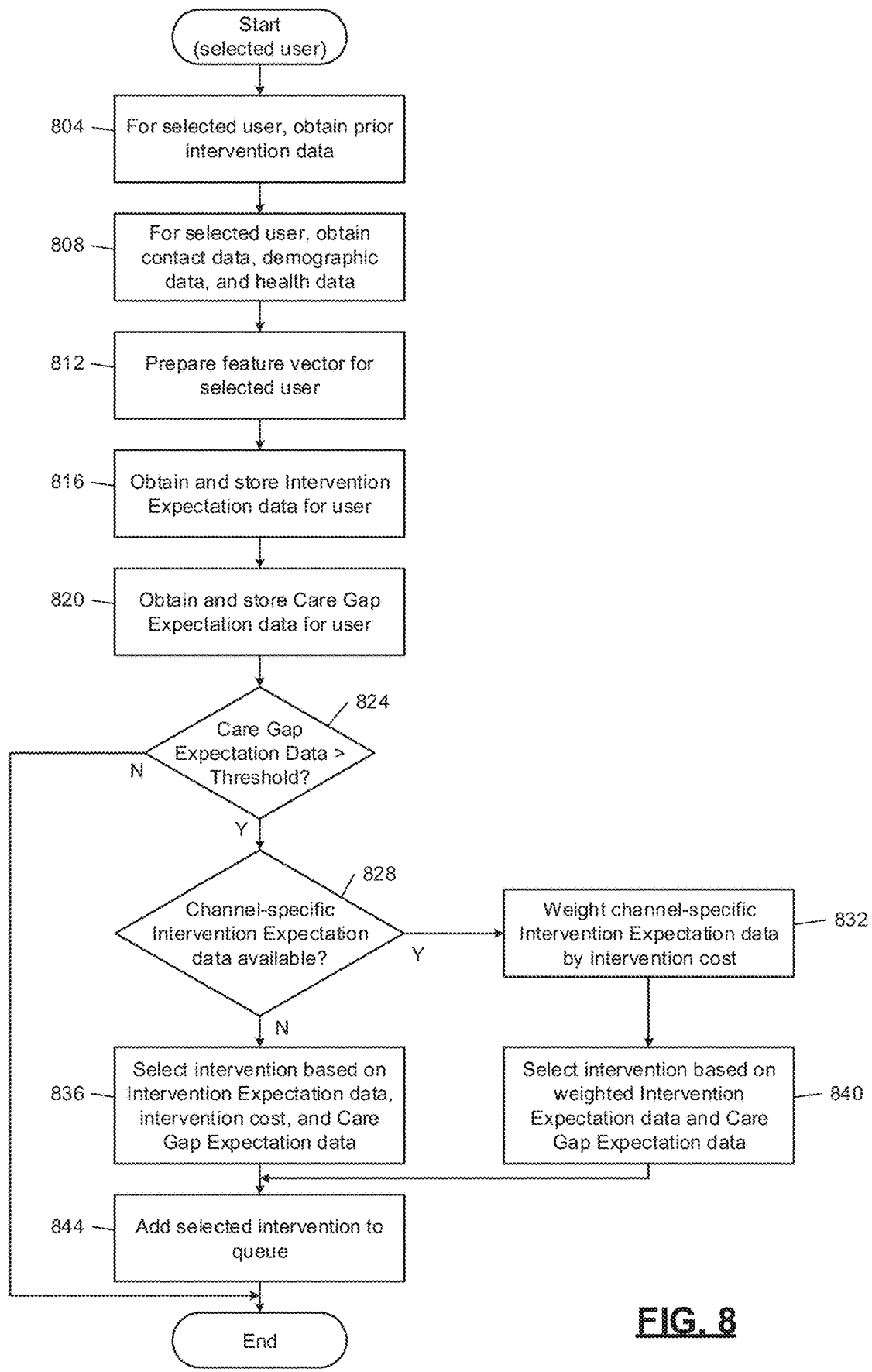
FIG. 8 is a flowchart showing example intervention determination for a specified user.
Figure 9A:
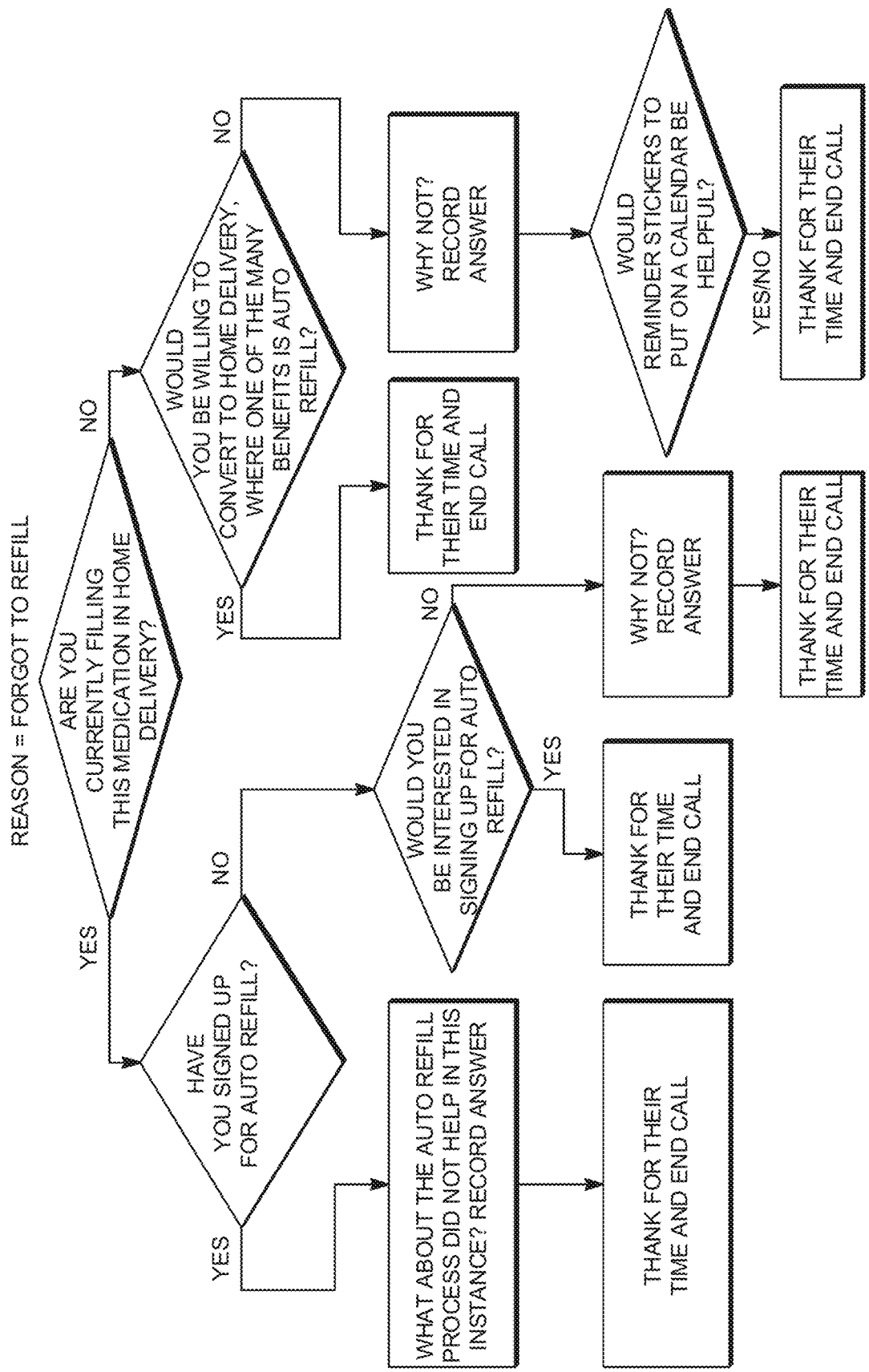
FIGS. 9A, 9B, 9C, 9D, and 9E are graphical representations of example intervention scripts for real-time interventions.
Figure 9B:
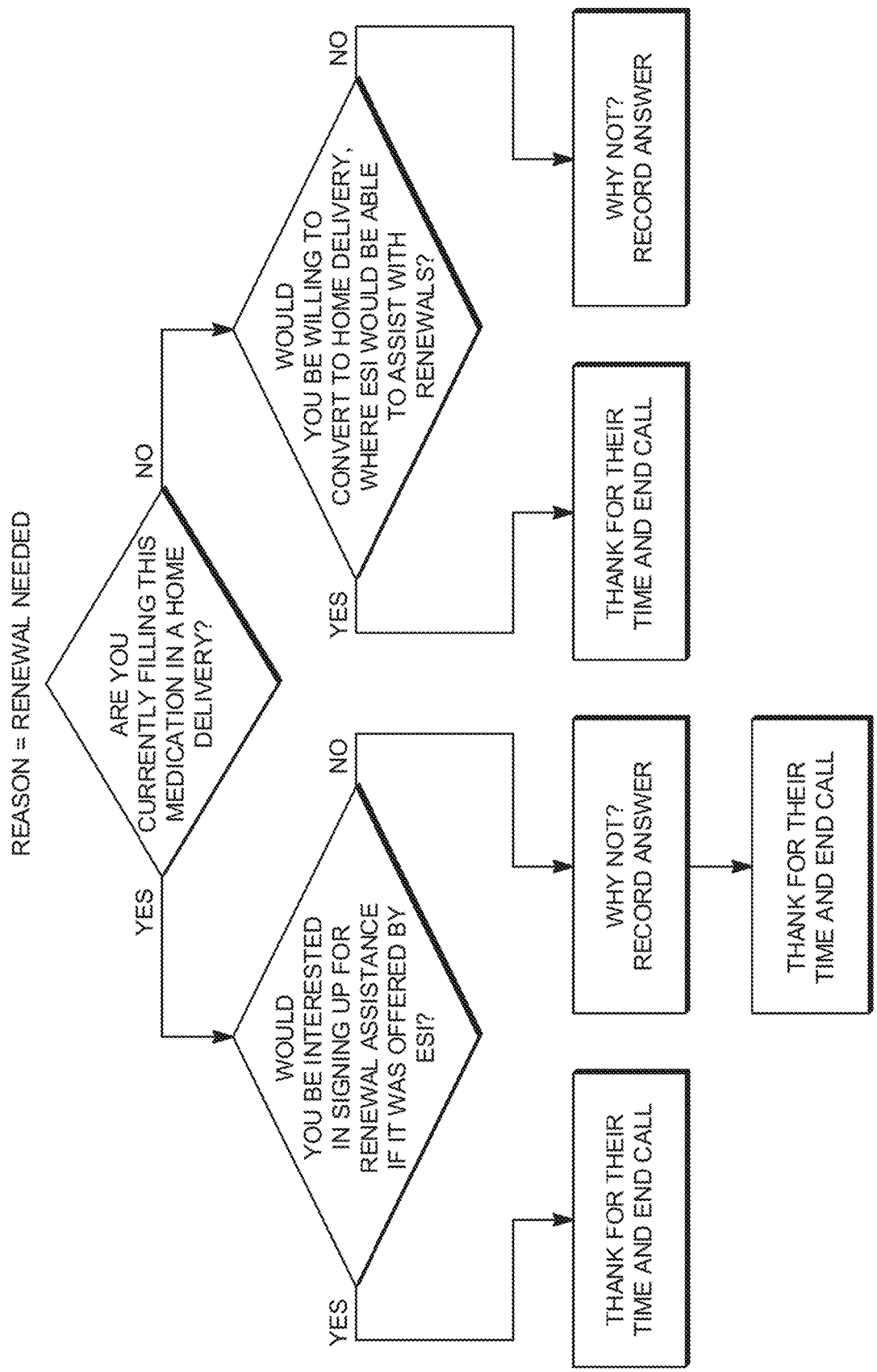
Figure 9C:
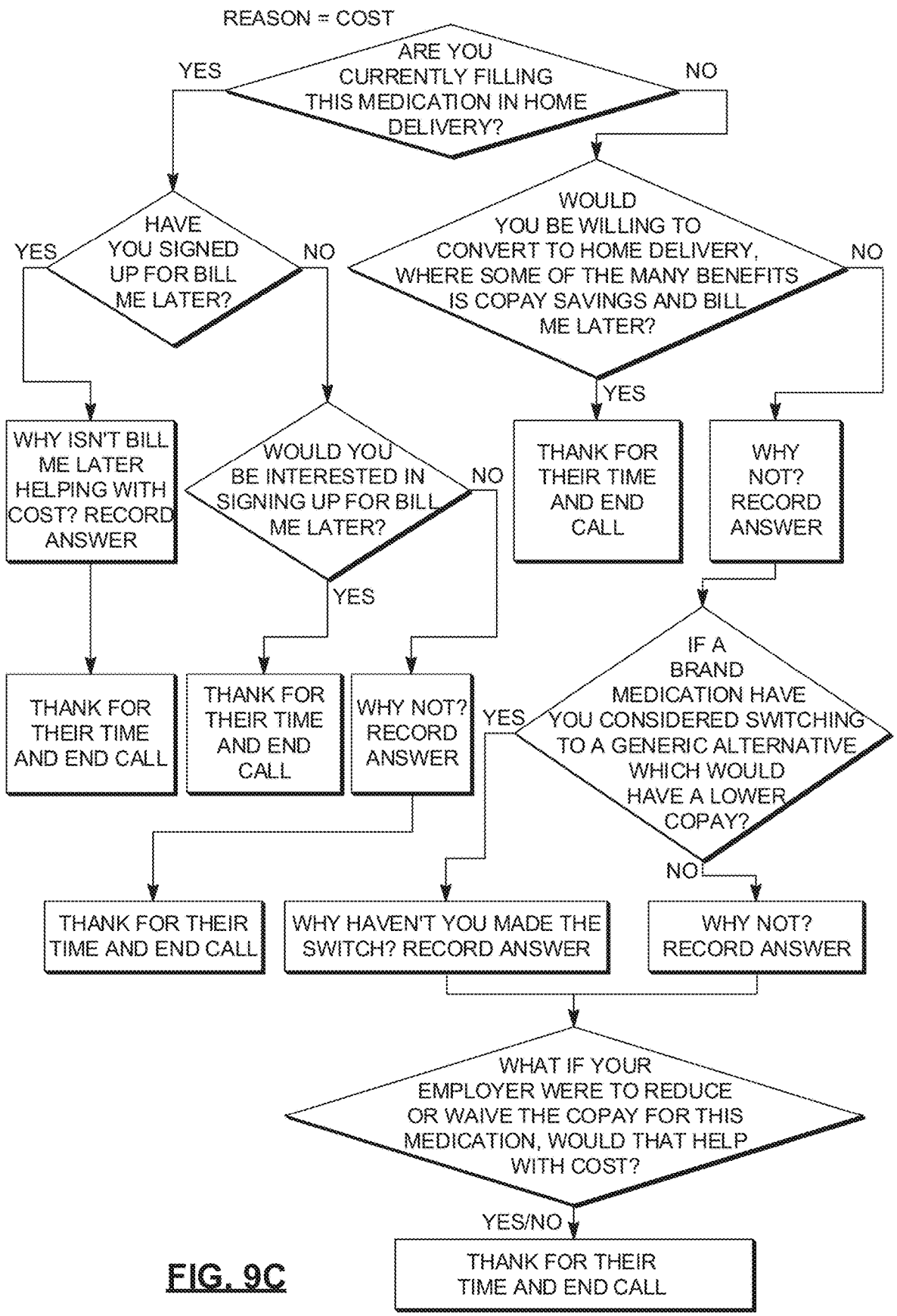
Figure 9D:
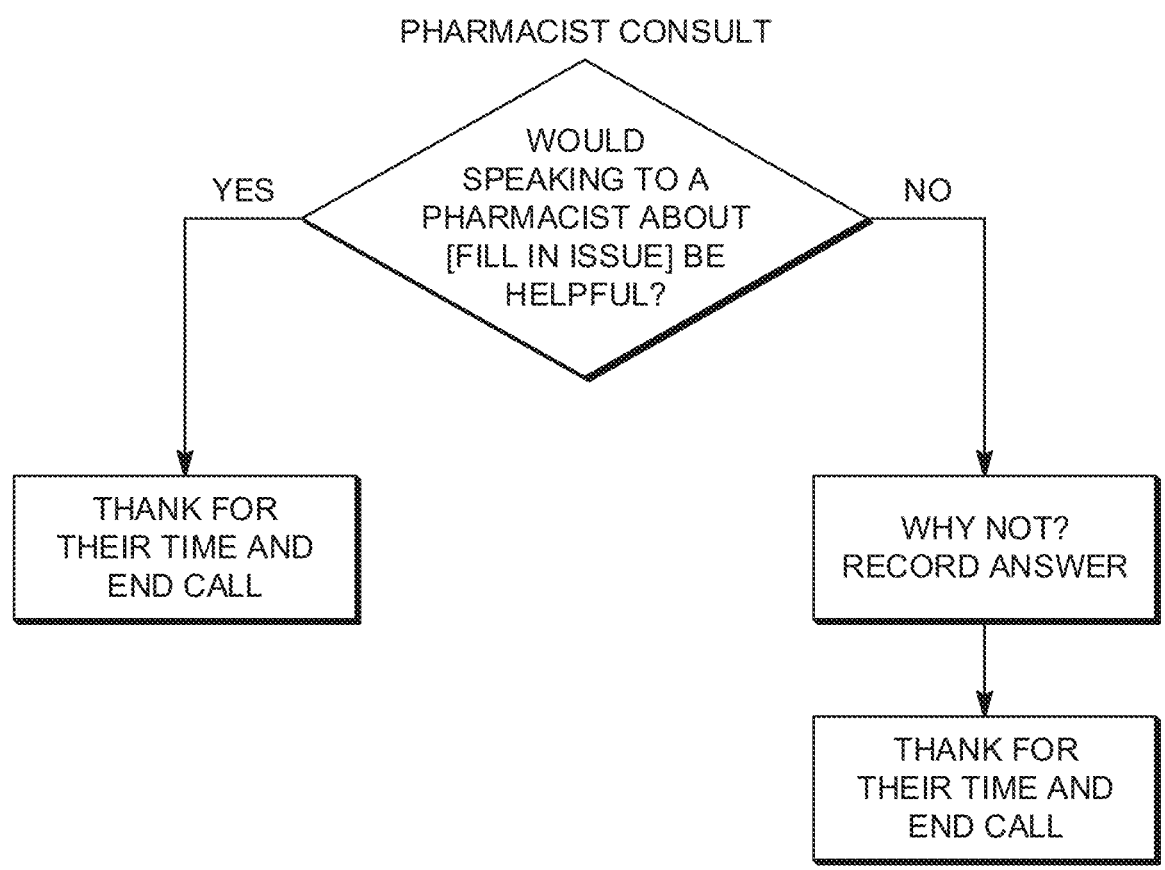
Figure 9E:
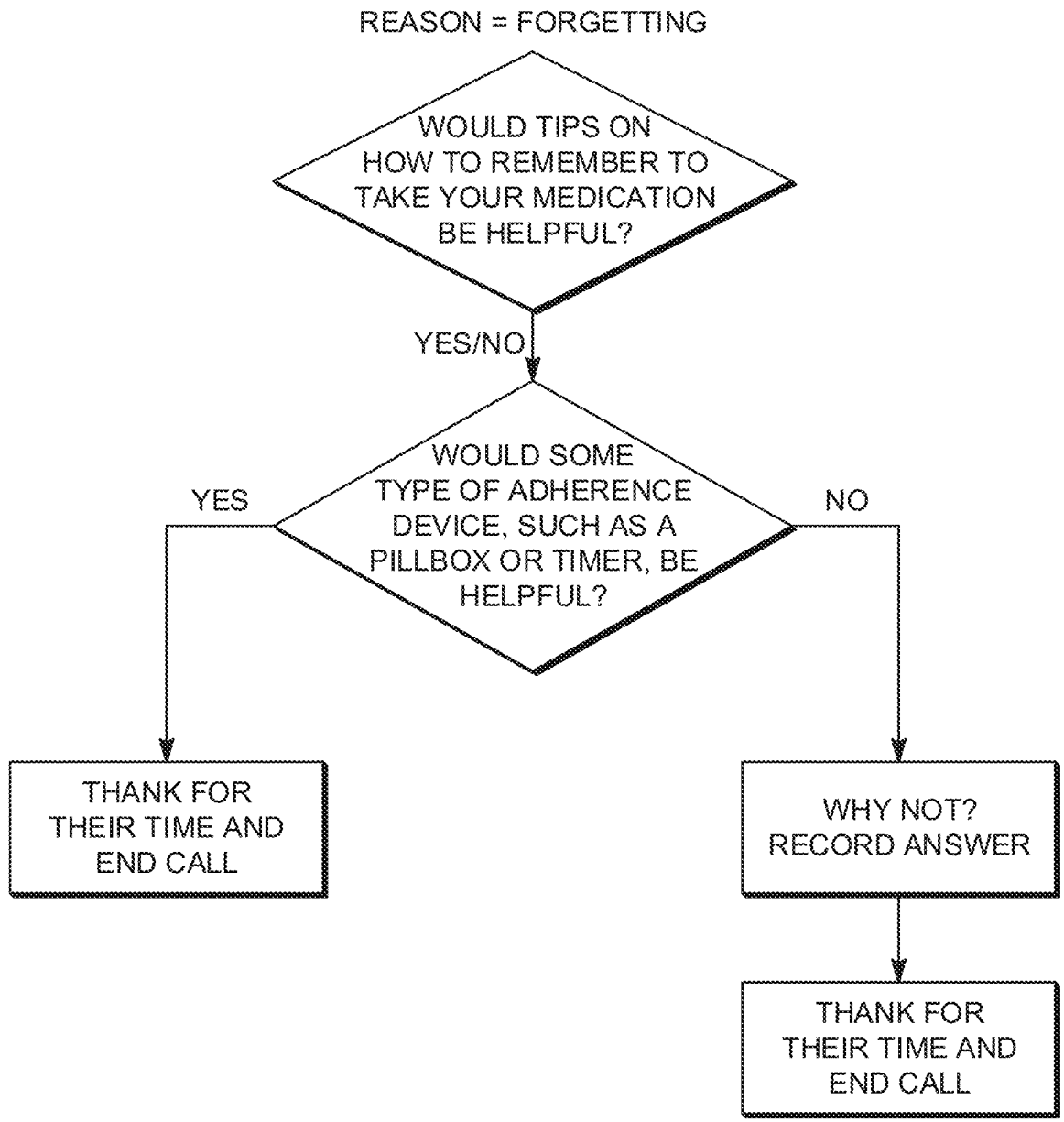

In FIG. 8, intervention analysis for a selected user begins at 804. For example, intervention analysis may be determined on a periodic basis, such as once per day, once per weekday, once per week, etc. In various implementations, the period may be selected by the client, such as the health insurer of the selected user.

At 804, for the selected user, control obtains prior intervention data. At 808, control obtains contact data, demographic data, and health data. At 812, control prepares a feature vector for the selected user based on the obtained data. At 816, control inputs the data to an intervention model, such as the intervention modeling circuit 416, and stores the intervention expectation data for the selected user (for example, into the model output data store 432 of FIG. 4). At 820, control inputs data into a care gap model and stores care gap expectation data for the user (for example, into the model output data store 432 of FIG. 4).

At 824, control determines whether the care gap expectation data exceeds a threshold. If so, control transfers to 828; otherwise, intervention is not required and control ends. At 828, control determines whether channel-specific intervention expectation data is available. If so, control transfers to 832; otherwise, control transfers to 836.

At 832, control weights the channel-specific intervention expectation data by the respective costs of the intervention. As an example, the cost of a telephone call from a specialist is substantially higher than the cost of a text message. Control continues at 840, where control selects an intervention for the user based on the weighted intervention expectation data and the care gap expectation data. For example, the above-described two-by-two grid or a combined score, also described above, may be employed. Control then continues at 844.

At 844, the selected intervention is added to the appropriate queue. For example, a queue for an automated intervention may be maintained by the automated intervention circuit 440 of FIG. 4. The automated queue may include a time and date at which the intervention should be executed (transmitted). For an intervention involving a specialist, the specialist management circuit 444 of FIG. 4 may maintain a queue for interventions to be executed by specialists. Following 844, control ends.

At 836, channel-specific intervention expectation data is not available and therefore an intervention is selected based on the single intervention expectation data and the care gap expectation data. In addition, the intervention may be selected according to the cost of the intervention. The intervention selection may be performed using, for example, the above-described two-by-two table. Control then continues at 844.

Channel-Specific Engagement Machine Learning Architecture

Figure 10:
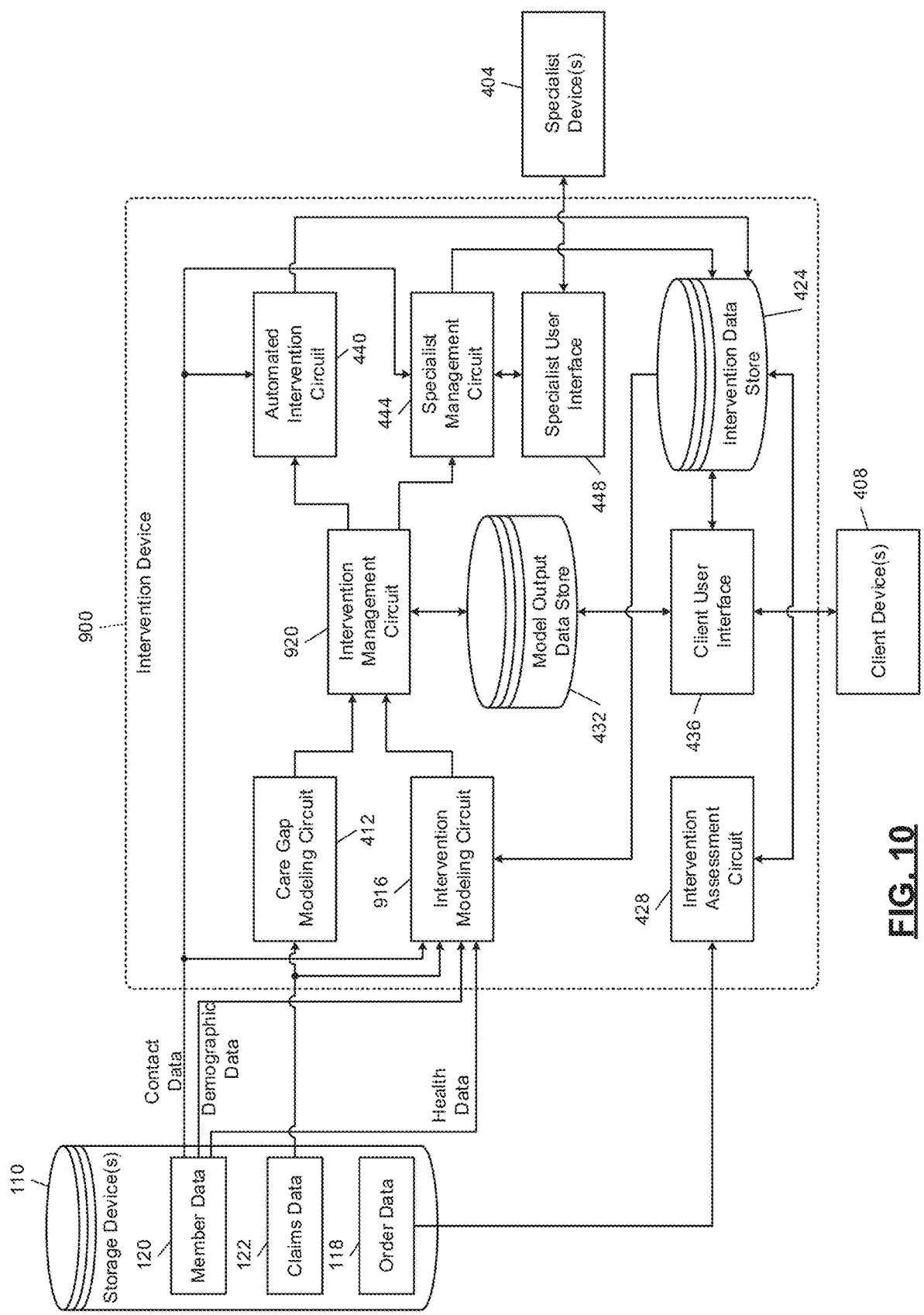
FIG. 10 is a functional block diagram of an example implementation of a channel-specific engagement machine learning architecture according to the principles of the present disclosure.

In FIG. 10, an example implementation of a channel-specific intervention device 900 includes a care gap modeling circuit 412 and an intervention modeling circuit 916. The care gap modeling circuit 412 develops a model indicating a likelihood of risk for a user, such as a risk of a gap in care. These estimations are provided to an intervention management circuit 920. The intervention modeling circuit 916 develops a model of the likelihood of user engagement with channel-specific interventions. The intervention engagement data is provided to the intervention management circuit 920.

The intervention modeling circuit 916 may receive, as inputs to the model, the claims data 122 for a specific user, demographic data of the user, contact data of the user, and health data of the user. The care gap modeling circuit 412 may also receive these inputs—for illustration purposes, the care gap modeling circuit 412 is shown in FIG. 10 as receiving just the claims data 122. Contact data may include indications of whether particular forms of contact (such as an email address) are present, and may also include more granular information, such as the domain of the email address. Demographic data may include, as examples, age and gender.

The claims data 122 may indicate historical data of when prescriptions were filled and may include information about intervals between refills. The intervention modeling circuit 916 also receives information about past interventions from an intervention data store 424. The intervention data store 424 tracks prior interventions, including email campaigns, phone calls, etc.

The intervention data store 424 may also store information about intervention outcomes. These outcomes may include verbal feedback provided during a phone call and may also include objective success measures from an intervention assessment circuit 428. The intervention assessment circuit 428 may receive the order data 118 and determine whether successes resulted from interventions.

For example, if an order is placed within 30 days of intervention, that may be classified as a success by the intervention assessment circuit 428. In various implementations, the business logic used by the intervention assessment circuit 428 to assess the success or failure of an intervention may be established by the business logic of the organization making the intervention. For example, an intervention that provides a discount for mail-order prescriptions may assess success only in response to receiving a mail-order script and not a retail script.

The intervention management circuit 920 stores care gap expectation data and intervention expectation data for users in a model output data store 432. A client user interface 436, which may be implemented in a web portal, allows the client devices 408 to access some or all of the information related to the care gap expectation data and intervention expectation data. The client user interface 436 may also provide access to information from the intervention data store 424, such as a list of past interventions for a user of interest.

The intervention management circuit 920 determines whether intervention is needed for a user and also determines the appropriate intervention. The intervention management circuit 920 assigns interventions to, in the example of FIG. 10, an automated intervention circuit 440 or a specialist management circuit 444. The automated intervention circuit 440 transmits automated interventions to users, such as emails, prerecorded calls, etc. The automated intervention circuit 440 may rely on contact data from the member data 120 and logs the interventions in the intervention data store 424.

The specialist management circuit 444 schedules specialist interactions. For example, specialists may include pharmacists, pharmacy technicians, and call center operators. The specialist management circuit 444 may prioritize and schedule specialist interventions. A specialist user interface 448, which may be implemented as a web portal, indicates to specialists using specialist devices 404 which users to contact. For example, a list of phone numbers to call may be presented to a specialist operating one of the specialist devices 404. The specialist user interface 448 allows the specialist to notate whether and what reaction was provided by the user and may also provide a script for the specialist to follow.

Figure 11:
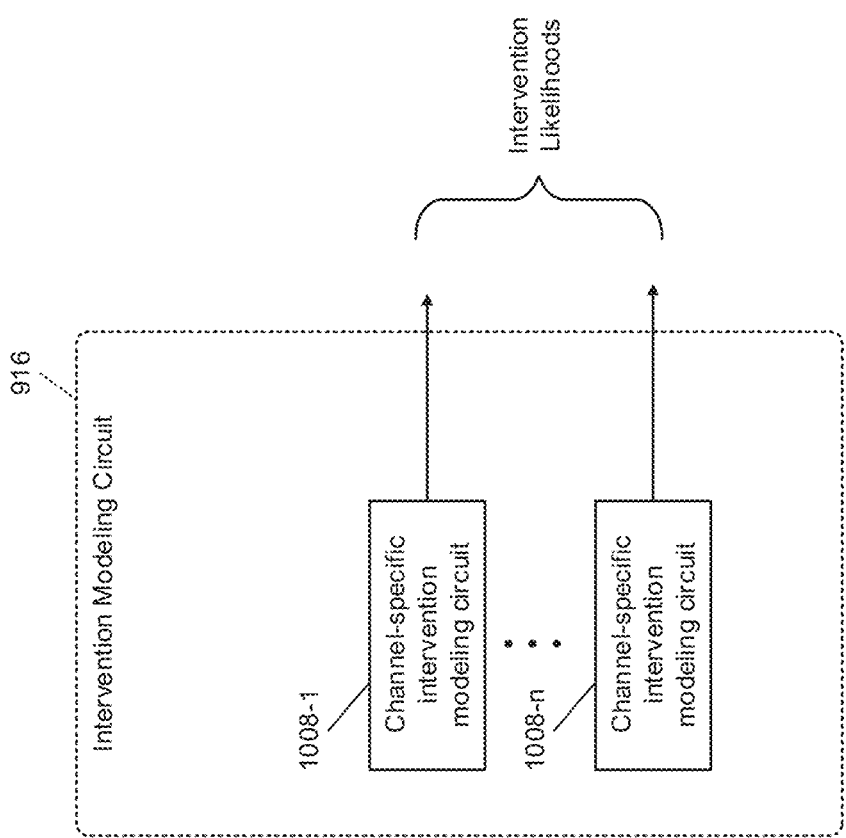
FIG. 11 is a functional block diagram of example channel-specific intervention modeling circuits.

In FIG. 11, an example implementation of the intervention modeling circuit 916 includes channel-specific intervention circuits 1008-1 . . . 1008-n (collectively, channel-specific intervention circuits 1008). Each of the channel-specific intervention circuits 1008 may be specific to a single channel of intervention or a class of intervention. For example, one class of intervention may be real-time, which includes a phone call (e.g., with a pharmacist or physician) or online chat, while a second class of intervention includes a unidirectional intervention such as an automated call, an email, a letter, or a text message.

Each channel-specific intervention circuit 1008 outputs an intervention likelihood for the channel intervention corresponding to that circuit 1008 (e.g., a likelihood that a patient will engage, become adherent, etc., if the patient is contacted via the channel intervention corresponding to that circuit 1008). The ensemble circuit 512 may output likelihoods of the user engaging with an intervention for each type of intervention.

For example, the intervention likelihood may be a value from 0 to 1, with a 1 indicating that the user is 100% likely to take action in response to a channel-specific intervention being executed (for example, a text message being sent or a call being placed). In various implementations, the intervention likelihood may be scored in one or more categories or ranges (e.g., high, medium or low), etc.

Each model of the channel-specific intervention circuits 1008 may be implemented using a logistic regression classifier based on determined feature vectors. In various implementations, some or all of the models may be implemented using a deep learning architecture (such as convolutional neural networks) that receives raw data that is not transformed into feature vectors. In various implementations, the deep learning architecture may essentially perform intrinsic feature engineering, ignoring data that is not correlated with engagement outcomes.

Figure 12:
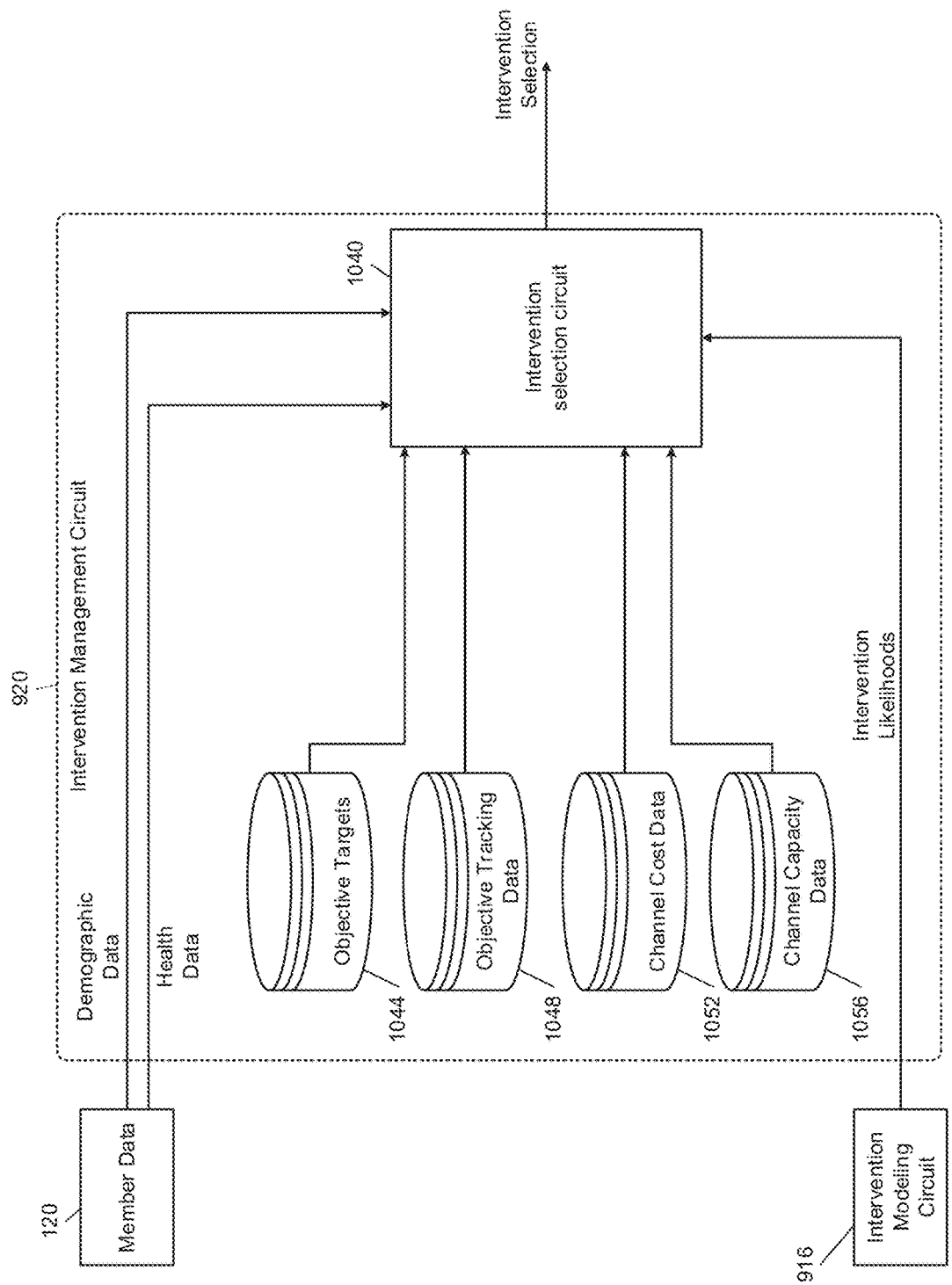
FIG. 12 is a functional block diagram of an example intervention management circuit.

In FIG. 12, an example implementation of the intervention management circuit 920 includes an intervention selection circuit 1040. The intervention selection circuit receives member data 120 for a patient, including demographic data and health data. The intervention selection circuit 1040 also receives intervention likelihoods from the intervention modeling circuit 916.

For example, the channel-specific intervention likelihoods (e.g., channel-specific intervention expectations) from each of the channel-specific intervention circuits 1008 may be supplied from the intervention modeling circuit 916 to the intervention selection circuit 1040, so the intervention selection circuit 1040 has likelihoods of engagement for the patient via each of the channels (e.g., a likelihood of engaging the patient via an automated call, a likelihood of engaging the patient via an email, a likelihood of engaging the patient via a letter, a likelihood of engaging the patient via a live call from a specialist such as a physician or pharmacist, etc.). In various implementations, a general or channel-agnostic likelihood of engagement for the patient overall may be supplied to the intervention selection circuit 1040.

As shown in FIG. 12, objective targets 1044 are supplied to the intervention selection circuit 1040. The objective targets 1044 may represent goals that an administrator of the channel-specific engagement machine learning architecture is trying to achieve. For example, the system administrator (e.g., a health plan provider) may offer a guarantee that an average of patients within a group (e.g., employees of a company) that use the channel-specific engagement machine learning architecture will be at least eighty percent adherent, a guarantee that at least fifty percent of identified non-adherent patients will become adherent, a guarantee that lab data (e.g., A1C test results) for a group of patients will be improved by a specified factor or will meet a specified threshold, etc.

Objective tracking data 1048 is supplied to the intervention selection circuit 1040 to monitor progress towards the targets, such as identifying how many patients are adherent relative to a guarantee, monitoring relevant lab test data for patients, etc. When the objective tracking data 1048 indicates that a group of patients are below the target, this may suggest that higher intervention likelihood channels should be used to increase the chance of patient engagement to return closer to the target. Objective tracking data 1048 that suggests a group of patients overall are above a target, may suggest that lower likelihood intervention channels may be used to free up intervention channels for other patients.

The intervention selection circuit 1040 also receives channel cost data 1052. The channel cost data 1052 allows the intervention selection circuit to weight the intervention likelihoods from the models of the channel-specific intervention circuits 1008 of the intervention modeling circuit based on how expensive each channel intervention is. For example, while live calls from a specialist may frequently have a higher intervention likelihood than an email, live calls from a specialist are also typically much more expensive than an email. Each live call from a physician may cost ten dollars, twenty dollars, etc., of the physician's time, while an automated call may use resources that cost pennies or less individually, and emails or text messages even less than that.

Similar to the channel cost data 1052, channel capacity data 1056 may also be supplied to the intervention selection circuit 1040. As an example, a pharmacist may only be able to complete one hundred live calls in a single day, while an automated system may be able to place thousands, and email or text messages may have even more capacity than that.

The intervention selection circuit 1040 may weight the intervention likelihoods from each different model of the channel-specific intervention circuits 1008 according to the relative costs and available capacity, in order to determine prioritization of which channels to use for which patients. For example, live calls may be prioritized for patients having very low intervention likelihoods in the other channels, while patients that have more equal likelihoods for each channel may be assigned to email or text message intervention channels to shift costs or allocate capacity to patients where the more expensive channels (e.g., automated calls and particularly live calls) may have greater relative effect in generating patient engagement. Although the present example uses four different intervention channels, other embodiments may include more or less channel-specific intervention circuits 1008 and associated models, other types of intervention channels, etc.

The intervention selection circuit 1040 may incorporate features from the member data 120 in order to prioritize selection of intervention channels for engaging a patient. The member data 120, intervention selection circuit 1040, etc., may identify or determine a cost to the patient to refill a prescription. For example, the circuit 1040 may incorporate a cost of the prescription, a co-pay or other information from a health plan of the patient, etc. Actions that will require a higher cost to the patient may suggest that a higher likelihood intervention channel should be used in an attempt to prevent the patient from delaying a refill further due to costs.

Similarly, the member data 120 may include pill burden information, such as a number of pills that the patient is currently taking. If the pill burden indicates a high number of current pills, this may suggest that a higher likelihood intervention channel should be used because the patient may have forgotten one of the many pills, the patient may be hesitant to refill the prescription and add to the number of pills that they must take, etc.

In various implementations, the member data 120 may include comorbidity information. If the patient has multiple diseases, this may suggest that a higher likelihood intervention channel should be used because the patient is at a higher risk of an adverse event such as a hospitalization event, a non-adherence event, a serious health event, etc. The patient comorbidity condition, pill burden, refill cost, etc., may be considered as user adherence factors.

The intervention selection circuit 1040 output an intervention selection that prioritizes one or more of the intervention channels based on the member data 120, the objective targets 1044, the objective tracking data 1048, the channel cost data 1052, and the intervention likelihoods from the intervention modeling circuit 916. The intervention selection circuit 1040 may include one or more models that balance the patient's intervention likelihoods from each of the channel-specific intervention circuits 1008, constraints such as costs and channel capacity, objective targets 1044, patient comorbidity data, etc., in order to optimize the selection of an intervention channel for the patient. The intervention selection circuit 1040 may include any suitable model(s) for prioritizing the intervention channel selection, such as a linear programming model, a logistic regression model, a random forest model, a decision tree model, a heuristic model, etc.

Channel-Specific Model Intervention Selection

Figure 13A:
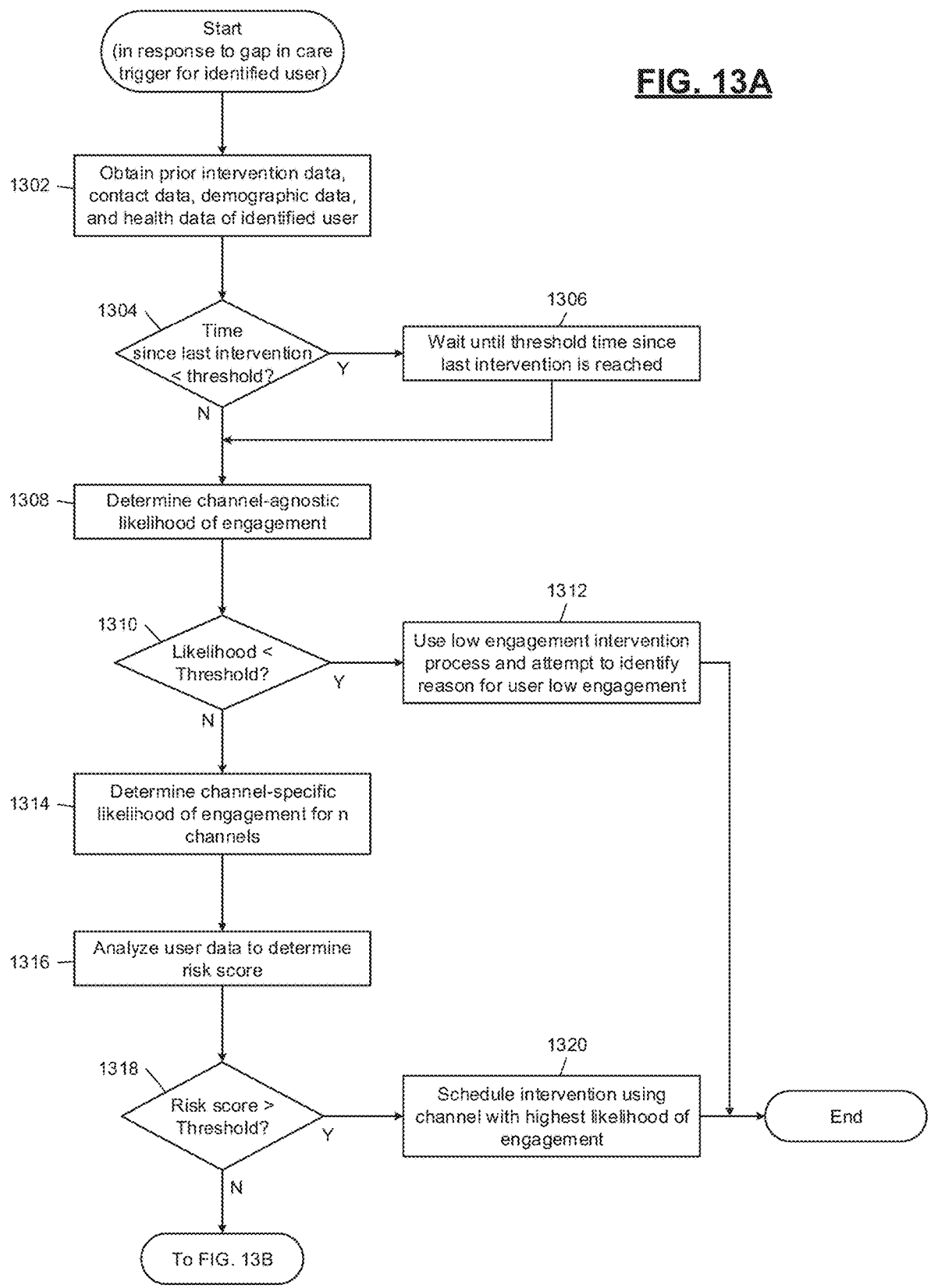
FIGS. 13A and 13B together are a flowchart showing example channel-specific intervention determination for a specified user.

In FIG. 13A, intervention analysis for a selected user begins at 1302. For example, intervention analysis may start in response to a gap in care trigger for an identified user, such as one or more business rules that identify a user having an outstanding prescription refill that is beyond an expected fill date by a threshold time period, etc. Alternatively, or in addition, intervention analysis may be determined on a periodic basis, such as once per day, once per weekday, once per week, etc. In various implementations, the period may be selected by the client, such as the health insurer of the selected user.

At 1302, control obtains prior intervention data, contact data, demographic data, and health data for the identified user (such as from the member data 120). At 1304, control determines whether a time period since the last intervention is greater than a threshold. If not, control proceeds to 1306 to wait until the threshold time since the last intervention is reached. For example, a minimum threshold time may be set between interventions, so a user is not receiving intervention engagements every day, etc.

If the time since the last intervention is greater than the threshold at 1304 (or if this is the first intervention), control proceeds to 1308 to determine a channel-agnostic likelihood of engagement. As described above, the channel-agnostic likelihood of engagement may indicate a general likelihood of a patient responding to an intervention using any channel.

If the channel-agnostic likelihood is less than a threshold at 1310, control proceeds to 1312 to use a low engagement intervention process and attempt to identify a reason for the user's lower engagement. For example, instead of using the basic intervention channels of the architecture, a specialist may identify other types of interventions that may be tried, additional patient data may be analyzed to identify alternative engagement outreach, etc.

In various implementations, control may attempt to identify a reason for the user's low overall engagement by storing and analyzing the user's member data 120. Identified or predicted reasons may be saved to improve the model, to improve intervention channel options, etc.

At 1314, control determines a channel-specific likelihood of engagement for n channels, which may involve use of the channel-specific intervention circuits 1008 of the intervention modeling circuit 916. As an example, the n channels may include a live call, an automated call, an email, a text message, etc.

Control analyzes user data to determine a risk score at 1316. The risk score may be indicative of a likelihood of a future adverse event for the user, such as a hospitalization event, a non-adherence event, a serious health event, etc. The user data may include data on a comorbidity condition for the user, a length or frequency of non-adherence, a type of disease of the user, past claims or medical history data, etc. If the risk score is greater than a threshold at 1318, control proceeds to 1320 to schedule an intervention using the channel with the highest likelihood of engagement. For example, if a live call has the highest likelihood of engagement for a user, and the user has a high risk of a future adverse event, a live call may be scheduled prior to weighing costs, capacity, etc., because of the user's high risk and the desire to engage with the user as much as possible to avoid the adverse event.

Figure 13B:
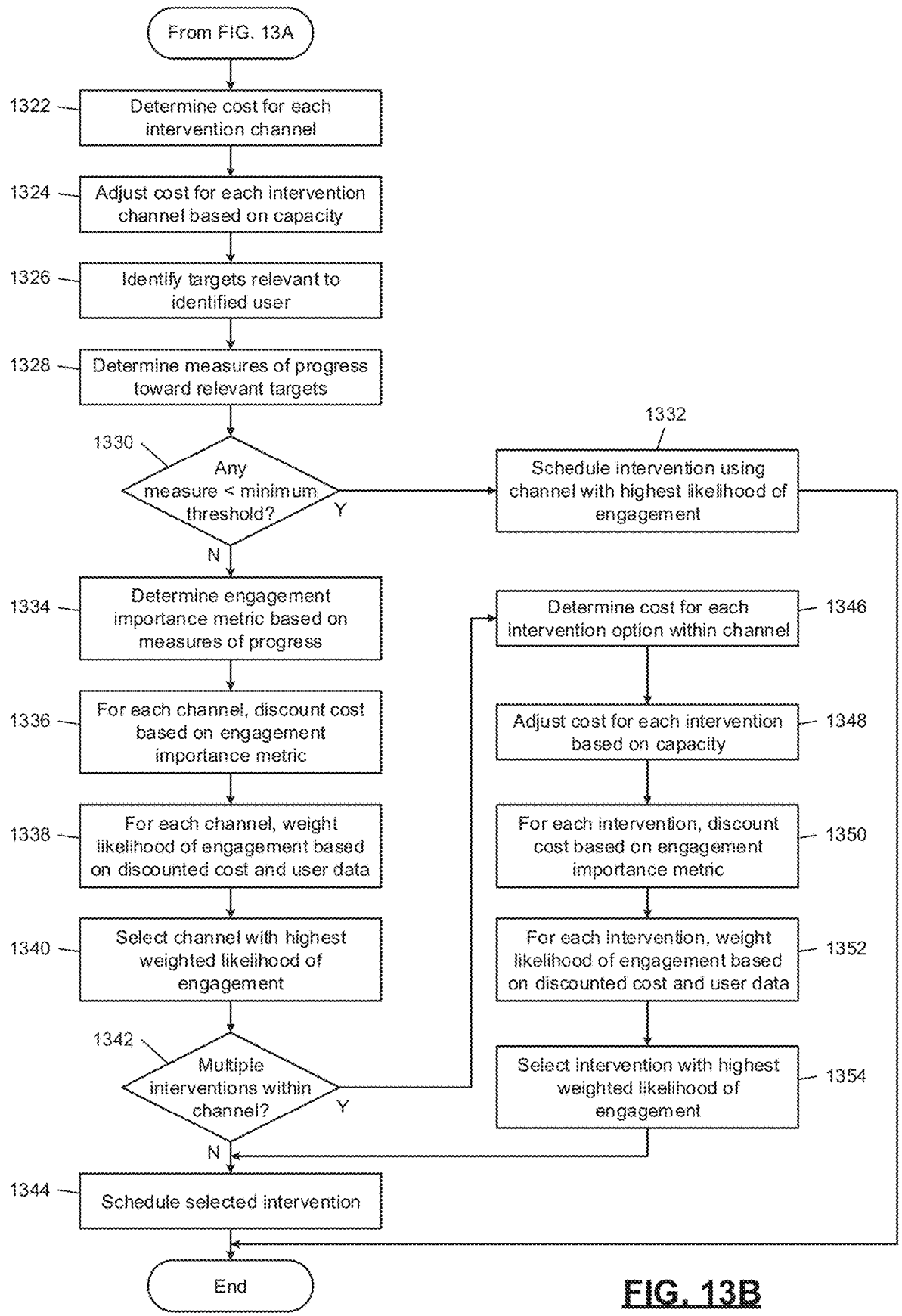

If the risk score is below the threshold, control proceeds to 1322 in FIG. 13B. At 1322, control determines a cost for each intervention channel, and adjusts the cost for each intervention channel based on capacity at 1324. Live calls may be assigned a cost based on the salary, hourly wage, etc., of a specialist that performs the live calls, divided by an average number of calls that the specialist can perform during a specified time period. The capacity is also taken into account where a shortage of live call specialists may adjust the cost upwards for live call interventions, while a large supply of available live call specialists may adjust the cost downwards for live call interventions. Similar cost and capacity analysis may be performed on other intervention channels, and the costs and capacities may be analyzed and adjusted using any suitable approaches.

At 1326, control identifies targets that are relevant to a user. The user may be part of a company health plan that has been offered a guarantee of at least eighty percent adherence for their members, the user may be part of a group of diabetes patients where a guarantee has been made to keep the average A1C test results for the group below a specified threshold (e.g., below 8), etc.

Control then proceeds to 1328 to determine measures of progress toward relevant targets. This may include analyzing objective targets 1044 and objective tracking data 1048. As an example, if a target adherence level for a group that the user belongs to is eighty percent, a measure of only seventy percent adherence for the group would indicate that the group is behind the target and therefore higher likelihood intervention channel(s) should be scheduled for the user to increase the progress toward the target. In contrast, a measure of ninety percent adherence for the group would indicate that the group is ahead of the target and therefore lower likelihood intervention channel(s) may be scheduled to allow for allocation of higher cost channels to other users.

At 1330, control determines whether any of the measures of progress for targets relevant to the user are less than a minimum threshold. If so, control proceeds to 1332 to schedule an intervention using the channel that has the highest likelihood of engagement. In the above example, if eighty percent adherence is the target value and seventy percent is a minimum threshold, a current group measure of only sixty percent adherence may require reaching out to the user with the highest likelihood channel in an attempt to more quickly raise the average adherence for the group back to the target or at least above the minimum threshold.

If there are not any measures of progress towards target(s) that are below a minimum threshold, control proceeds to 1334 to determine an engagement importance metric based on measures of progress. For example, if the measure of progress is below the target, the engagement importance metric may have a higher value because it is more important to engage the user to bring the measure of progress back up for the relevant group. Conversely, if the measure of progress is above the target, the engagement importance metric may have a lower value because it is less important to engage the user as the measure of progress is already high.

At 1336, control discounts a cost of each channel based on the engagement importance metric. If the engagement importance metric has a high value (e.g., it is more important than average to engage the user to try to raise the measure of progress towards the target), the cost of each channel may be discounted by a larger amount because the system is more willing to prioritize the expensive channels due to the need to raise the measure of progress. In contrast, if the engagement importance metric has a low value (e.g., it is less important than average to engage the user because the measure of progress is already above the target), the cost of each channel may not be discounted at all, or by only a small amount, because the system has a lower priority for engaging this user and may prefer to allocate higher cost resources to users in groups having lower measures of progress towards targets.

Control then proceeds to 1338 to weight the channel-specific likelihood of engagement for each channel, based on the discounted cost and the user data. The weighting may take into account any user data, including member data 120, such as a refill cost to the user, a pill burden of the user, comorbidity information about the user, etc. This can be combined with the discounted costs determined at 1336 (which take into account resource and cost constraints for the different channels, in addition to measures of progress toward relevant cost), in order to adjust weights of the channel-specific likelihoods determined at 1314 (e.g., intervention likelihoods from the channel-specific intervention circuits 1008).

At 1340, control selects the channel with the highest weighted likelihood of engagement. For example, the intervention selection circuit 1040 may include one or more models that perform the weighting adjustment of step 1338 (in addition to any other suitable elements of flow of FIGS. 13A and 13B), and the circuit 1040 may then select the channel that has the highest weighted likelihood at 1340. The circuit 1040 may include any suitable model(s), such as a linear programming optimizer model, a logistic regression model, a decision tree model, a random forest model, a heuristic model, etc.

If the selected channel does not include multiple interventions at 1342, control proceeds to schedule the selected intervention at 1344. However, some channels may include multiple interventions within the single channel. For example, live or automated calls may follow different predefined scripts depending on how the user responds during the call, emails or text messages may have different text options, etc.

If the selected channel has multiple intervention options at 1342, control proceeds to 1346 to determine a cost for each intervention option within each channel. For example, a longer or more complex call script may increase the likelihood of engaging a user even though the longer or more complex call script is more costly due to the increased time for a specialist to be on the call. FIGS. 9A-9E illustrate example call scripts of various complexity and length. In some channels, the cost for each intervention option may be approximately the same (e.g., an email or text message cost is similar regardless of the text of the message).

At 1348, control adjusts the cost for each intervention option based on the available capacity. At 1350, control discounts the cost of each intervention option based on the engagement importance metric (e.g., the engagement importance metric determined at 1334). Adjusting and discounting the cost of each intervention option based on capacity and the engagement importance metric may be similar to steps 1324 and 1336, but applied to each intervention option within a single channel.

At 1352, control weights, for each intervention option within the selected channel, the likelihood of engagement based on the determined discounted cost and the user data. Control then selects the intervention option with the highest weighted likelihood of engagement at 1354. For example, multiple variations of scripts, message texts, etc., may be generated and test for success rates over time (e.g., success of producing user engagement, etc.).

In addition to determining a channel-specific likelihood of engagement, the channel-specific intervention circuits 1008 may also output engagement likelihoods for each intervention option within a channel. Control (e.g., the intervention selection circuit 1040) then selects the intervention option with the highest likelihood of engagement at 1354 and schedules the selected intervention option at 1344.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. The phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computer-implemented method comprising:
   generating an intervention model for a population of users based on contact data for each of the population of users, demographic data for each of the population of users, and engagement data indicating successfulness of prior interventions for each of the population of users, wherein:
      each prior intervention corresponds to one of multiple engagement channels, and
      the intervention model includes multiple channel-specific models, each corresponding to a respective one of the multiple engagement channels; and
   for a first user of the population of users:
      obtaining first data related to the first user, wherein:
         the first data includes at least one of contact data of the first user, demographic data of the first user, and engagement data indicating successfulness of prior interventions with the first user, and each prior intervention with the first user is associated with one of the multiple engagement channels;
      supplying the obtained first data as input to the intervention model to determine multiple channel-specific intervention expectations, wherein each channel-specific intervention expectation indicates a likelihood that the first user will take action in response to an intervention being executed using the engagement channel corresponding to the channel-specific intervention expectation;
      determining a likelihood of a gap in care for the first user; and
      in response to the gap in care likelihood exceeding a minimum threshold:
         selecting a first intervention according to the channel-specific intervention expectation that has a highest determined value; and
         scheduling the selected first intervention for execution;
   wherein at least a selected model of the multiple channel-specific models is a machine learning model, wherein the selected model is generated by:
      determining principal components for features of a training set,
      associating each feature of the training set with a principal component,
      selecting the features of the training set most closely correlated with principal components,
      performing a regression analysis on the selected features to determine a subset of the selected features that are most closely correlated with a model target,
      training the machine learning model with the subset of the selected features of the training set,
      applying the trained machine learning model to feature vectors of a verification set to determine a predicted likelihood of engagement, and
      in response to the predicted likelihood of engagement being within a predetermined threshold, saving the trained machine learning model as the selected model.

2. The method of claim 1 wherein the multiple engagement channels include at least two of a real-time communication with the first user by a specialist, a call to the first user by an automated call system, an email to the first user, and a text message to the first user.

3. The method of claim 2 wherein:
   at least one of the multiple engagement channels includes multiple intervention options within the engagement channel;
   selecting the first intervention includes selecting a first one of the multiple intervention options within the engagement channel that has a highest intervention expectation among the intervention options; and
   scheduling the first intervention includes scheduling the selected first one of the multiple intervention options within the engagement channel.

4. The method of claim 1 wherein:
   the intervention model includes a channel-agnostic intervention model that determines a general intervention expectation indicating a likelihood that the first user will take action in response to any intervention being executed using any of the engagement channels; and
   the method further comprises, in response to the general intervention expectation being below a specified threshold, initiating a low engagement intervention process and identifying at least one reason for low engagement of the first user.

5. The method of claim 1 further comprising, in response to determining that a time elapsed since a most recent intervention for the first user is less than a specified delay threshold, waiting until the specified delay threshold has elapsed prior to selecting the first intervention.

6. The method of claim 1 further comprising:
identifying one or more targets relevant to the first user;
determining a measure of progress toward at least one of the identified targets;
determining an engagement importance metric based on the determined measure of progress; and
weighting the channel-specific intervention expectations according to the determined engagement importance metric prior to selecting the first intervention.

7. The method of claim 6 wherein scheduling the first intervention includes, in response to determining that the measure of progress is less than a specified minimum threshold, scheduling an intervention corresponding to the channel-specific intervention expectation that has a highest determined value prior to weighting.

8. The method of claim 1 further comprising:
determining a cost of engagement for each of the multiple engagement channels;
determining a channel capacity for each of the multiple engagement channels; and
weighting the channel-specific intervention expectations according to the determined costs of engagement and channel capacities prior to selecting the first intervention.

9. The method of claim 1 further comprising determining at least one user adherence factor associated with the first user, and weighting the channel-specific intervention expectations according to the determined user adherence factor prior to selecting the first intervention.

10. The method of claim 9 wherein the at least one user adherence factor includes at least one of a prescription refill cost to the first user, a pill burden of the first user, and a comorbidity condition of the first user.

11. The method of claim 10 wherein scheduling the first intervention includes, in response to the comorbidity condition of the first user indicating a future adverse event risk that is higher than a specified threshold, scheduling an intervention corresponding to the channel-specific intervention expectation that has a highest determined value prior to weighting.

12. The method of claim 1 further comprising tracking success of the selected first intervention based on a medication possession ratio (MPR), wherein the MPR is calculated as a number of days of a prescription currently in possession of the first user divided by a number of total days initially supplied with the prescription.

13. A system comprising:
memory configured to store computer-executable instructions and an intervention model for a population of users based on contact data for each of the population of users, demographic data for each of the population of users, and engagement data indicating successfulness of prior interventions for each of the population of users, wherein each prior intervention corresponds to one of multiple engagement channels, and the intervention model includes multiple channel-specific models, each corresponding to a respective one of the multiple engagement channels; and
at least one processor configured to execute the instructions, wherein the instructions include:
for a first user of the population of users:
obtaining first data related to the first user, wherein:
the first data includes at least one of contact data of the first user, demographic data of the first user, and engagement data indicating successfulness of prior interventions with the first user, and
each prior intervention with the first user is associated with one of the multiple engagement channels;
supplying the obtained first data as input to the intervention model to determine multiple channel-specific intervention expectations, wherein each channel-specific intervention expectation indicates a likelihood that the first user will take action in response to an intervention being executed using the engagement channel corresponding to the channel-specific intervention expectation;
determining a likelihood of a gap in care for the first user; and
in response to the gap in care likelihood exceeding a minimum threshold:
selecting a first intervention according to the channel-specific intervention expectation that has a highest determined value; and
scheduling the selected first intervention for execution;
wherein at least a selected model of the multiple channel-specific models is a machine learning model, wherein the selected model is generated by:
determining principal components for features of a training set,
associating each feature of the training set with a principal component,
selecting the features of the training set most closely correlated with principal components,
performing a regression analysis on the selected features to determine a subset of the selected features that are most closely correlated with a model target,
training the machine learning model with the subset of the selected features of the training set,
applying the trained machine learning model to feature vectors of a verification set to determine a predicted likelihood of engagement, and
in response to the predicted likelihood of engagement being within a predetermined threshold, saving the trained machine learning model as the selected model.

14. The system of claim 13 wherein the multiple engagement channels include at least two of a real-time communication with the first user by a specialist, a call to the first user by an automated call system, an email to the first user, and a text message to the first user.

15. The system of claim 14 wherein:
at least one of the multiple engagement channels includes multiple intervention options within the engagement channel;
selecting the first intervention includes selecting a first one of the multiple intervention options within the engagement channel that has a highest intervention expectation among the intervention options; and
scheduling the first intervention includes scheduling the selected first one of the multiple intervention options within the engagement channel.

16. The system of claim 13 wherein:
the intervention model includes a channel-agnostic intervention model that determines a general intervention expectation indicating a likelihood that the first user will take action in response to any intervention being executed using any of the engagement channels; and the instructions include in response to the general intervention expectation being below a specified threshold, initiating a low engagement intervention process and identifying at least one reason for low engagement of the first user.

17. The system of claim 13 wherein the instructions further include, in response to determining that a time elapsed since a most recent intervention for the first user is less than a specified delay threshold, waiting until the specified delay threshold has elapsed prior to selecting the first intervention.

18. The system of claim 13 wherein the instructions further include:
    identifying one or more targets relevant to the first user;
    determining a measure of progress toward at least one of the identified targets;
    determining an engagement importance metric based on the determined measure of progress; and
    weighting the channel-specific intervention expectations according to the determined engagement importance metric prior to selecting the first intervention.

19. The system of claim 18 wherein scheduling the first intervention includes, in response to determining that the measure of progress is less than a specified minimum threshold, scheduling an intervention corresponding to the channel-specific intervention expectation that has a highest determined value prior to weighting.

20. The system of claim 13 wherein the instructions further include:
    determining a cost of engagement for each of the multiple engagement channels;
    determining a channel capacity for each of the multiple engagement channels; and
    weighting the channel-specific intervention expectations according to the determined costs and channel capacities prior to selecting the first intervention.

* * * * *